(12) United States Patent
Kornowski et al.

(10) Patent No.: US 10,039,896 B2
(45) Date of Patent: Aug. 7, 2018

(54) DEPLOYMENT MECHANISM FOR BODY VESSEL INSERTION DEVICES

(75) Inventors: Ran Kornowski, Ramat-HaSharon (IL); Dvir Keren, Tel Aviv (IL)

(73) Assignee: Nitiloop Ltd., Herzlia (IL)

( * ) Notice: Subject to any disclaimer, the term of this patent is extended or adjusted under 35 U.S.C. 154(b) by 0 days.

(21) Appl. No.: 14/119,873

(22) PCT Filed: May 23, 2012

(86) PCT No.: PCT/IL2012/050184
§ 371 (c)(1),
(2), (4) Date: Nov. 24, 2013

(87) PCT Pub. No.: WO2012/160562
PCT Pub. Date: Nov. 29, 2012

(65) Prior Publication Data
US 2014/0128844 A1    May 8, 2014

Related U.S. Application Data

(60) Provisional application No. 61/488,830, filed on May 23, 2011.

(51) Int. Cl.
*A61M 25/00*    (2006.01)
*A61M 25/04*    (2006.01)
(Continued)

(52) U.S. Cl.
CPC ....... *A61M 25/001* (2013.01); *A61B 18/1492* (2013.01); *A61M 25/0009* (2013.01);
(Continued)

(58) Field of Classification Search
CPC ...... A61B 18/1492; A61B 2017/22042; A61B 2017/22044; A61B 2017/22047;
(Continued)

(56) References Cited

U.S. PATENT DOCUMENTS 5,071,407 A    12/1991    Termin et al.
5,405,380 A    4/1995    Gianotti et al.
(Continued)

FOREIGN PATENT DOCUMENTS

EP    0592726    4/1994
JP    06-197975    7/1994
(Continued)

OTHER PUBLICATIONS

International Search Report and the Written Opinion dated Aug. 29, 2012 From the International Searching Authority Re. Application No. PCT/IL2012/050184.
(Continued)

*Primary Examiner* — Bhisma Mehta
*Assistant Examiner* — Brandy S Lee

(57) ABSTRACT

An aspect of some embodiments of the invention relates to a microcatheter comprising a deployment element disposed about around at least a portion of an exterior of a distal end of the microcatheter, the deployment element configured for repeatedly expanding and collapsing, the distal end arranged to allow forward or reverse axial displacement while the deployment element maintains a position, the deployment element arranged for positioning the microcatheter distal end approximately in the middle of a vessel. A method of traversing tortuous vessels using the microcatheter, in accordance with an exemplary embodiment of the invention, is also described.

25 Claims, 19 Drawing Sheets

(51) Int. Cl.
  *A61B 18/14* (2006.01)
  *A61B 17/22* (2006.01)
  *A61B 18/00* (2006.01)
  *A61B 90/00* (2016.01)
(52) U.S. Cl.
  CPC ... *A61M 25/04* (2013.01); *A61B 2017/22042* (2013.01); *A61B 2017/22044* (2013.01); *A61B 2017/22047* (2013.01); *A61B 2017/22094* (2013.01); *A61B 2018/00422* (2013.01); *A61B 2018/00577* (2013.01); *A61B 2018/1475* (2013.01); *A61B 2090/3966* (2016.02); *A61M 25/0082* (2013.01); *A61M 2025/0042* (2013.01); *A61M 2025/0079* (2013.01); *Y10T 29/49826* (2015.01)
(58) Field of Classification Search
  CPC .......... A61B 2017/22094; A61B 2018/00422; A61B 2018/00577; A61B 2018/1475; A61B 2019/5466; A61B 2090/3966; A61M 2025/0042; A61M 2025/0079; A61M 25/0009; A61M 25/001; A61M 25/0082; A61M 25/04; A61M 2025/0681; A61M 2025/0293; A61M 25/00
  See application file for complete search history.

(56) References Cited

U.S. PATENT DOCUMENTS

| | | | |
|---|---|---|---|
| 5,456,667 A | 10/1995 | Ham et al. | |
| 5,509,900 A | 4/1996 | Kirkman | |
| 5,928,260 A * | 7/1999 | Chin | A61B 17/12022 604/107 |
| 6,059,812 A * | 5/2000 | Clerc | A61N 5/1002 600/3 |
| 6,059,814 A * | 5/2000 | Ladd | A61B 17/221 606/200 |
| 6,168,604 B1 | 1/2001 | Cano | |
| 7,169,160 B1 | 1/2007 | Middleman et al. | |
| 2001/0012951 A1 | 8/2001 | Bates et al. | |
| 2005/0085846 A1 | 4/2005 | Carrison et al. | |
| 2007/0123925 A1* | 5/2007 | Benjamin | A61M 25/0041 606/194 |
| 2007/0299497 A1 | 12/2007 | Shaolian et al. | |
| 2009/0264859 A1 | 10/2009 | Mas | |
| 2011/0022038 A1* | 1/2011 | Seshadri | A61B 17/3207 606/7 |

FOREIGN PATENT DOCUMENTS

| | | |
|---|---|---|
| JP | 10-263096 | 10/1998 |
| JP | 2000-504595 | 4/2000 |
| JP | 2002-513646 | 5/2002 |
| JP | 2003-509150 | 3/2003 |
| JP | 2007-508902 | 4/2007 |
| WO | WO 95/10317 | 4/1995 |
| WO | WO 97/27808 | 8/1997 |
| WO | WO 99/56801 | 11/1999 |
| WO | WO 2012/160562 | 11/2012 |

OTHER PUBLICATIONS

International Preliminary Report on Patentability dated Dec. 5, 2013 From the International Bureau of WIPO Re. Application No. PCT/IL2012/050184.
Notification of Office Action and Search Report dated Mar. 26, 2015 From The State Intellectual Property Office of the People's Republic of China Re. Application No. 201280036386.0 and Its Summary in English.
Notice of Reason for Rejection dated Mar. 8, 2016 From the Japanese Patent Office Re. Application No. 2014-512003 and Its Translation Into English.
Communication Pursuant to Article 94(3) EPC dated Sep. 15, 2015 From the European Patent Office Re. Application No. 12735054.4.
Notice of Reason for Rejection dated Apr. 4, 2017 From the Japanese Patent Office Re. Application No. 2014-512003 and Its Translation Into English. (6 Pages).
Office Action dated Jan. 5, 2017 From the Israel Patent Office Re. Application No. 229592 and Its Translation Into English. (6 Pages).
Notice of Reason for Rejection dated Mar. 8, 2016 From the Japanese Patent Office Re. Application No. 2014-512003.
Communication Pursuant to Article 94(3) EPC dated May 15, 2018 From the European Patent Office Re. Application No. 12735054.4. (4 Pages).
Notification of Office Action dated May 2, 2018 From the State Intellectual Property Office of the People's Republic of China Re. Application No. 201610089901.1 and Its Translation Into English. (5 Pages).
Requisition by the Examiner dated Apr. 5, 2018 From the Innovation, Science and Economic Development Canada, Canadian Intellectual Property Office Re. Application No. 2,835,048. (4 Pages).

* cited by examiner

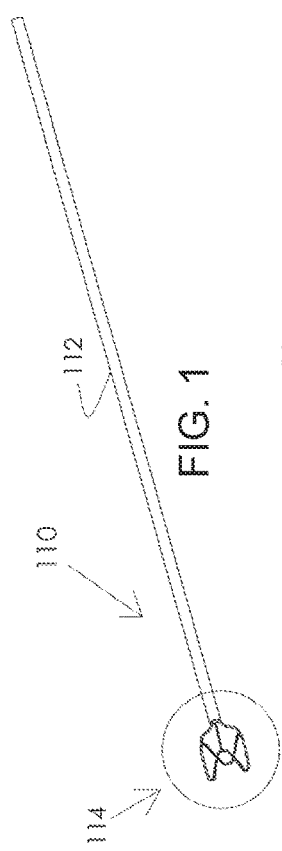
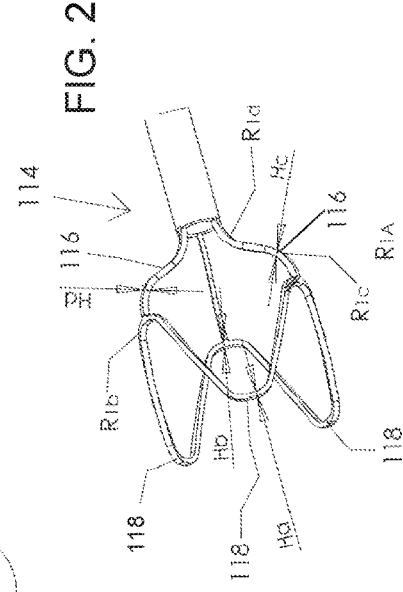
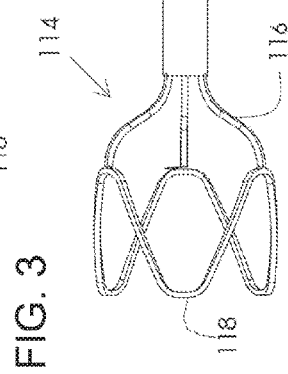
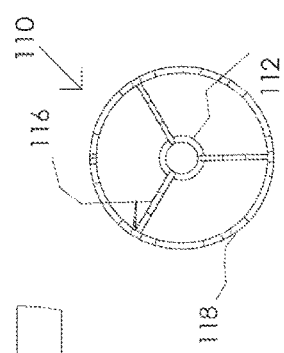

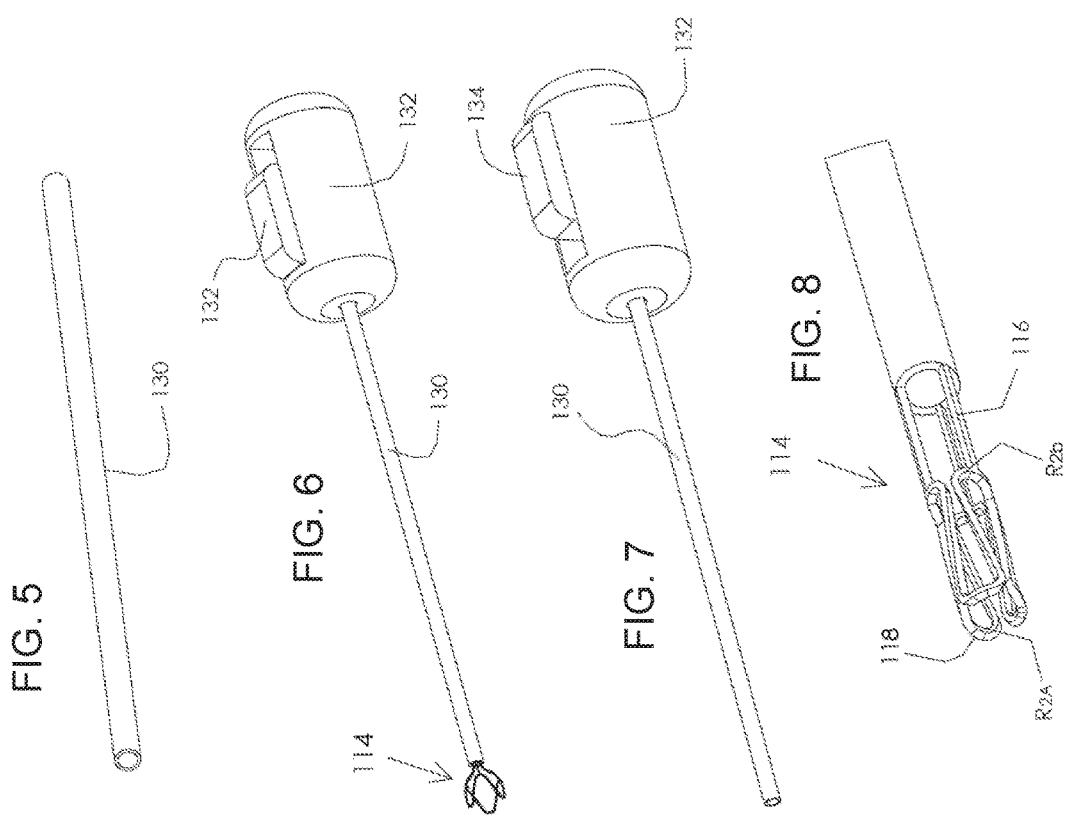

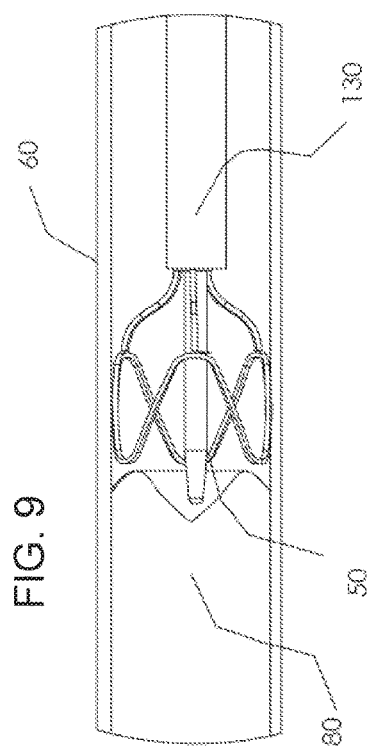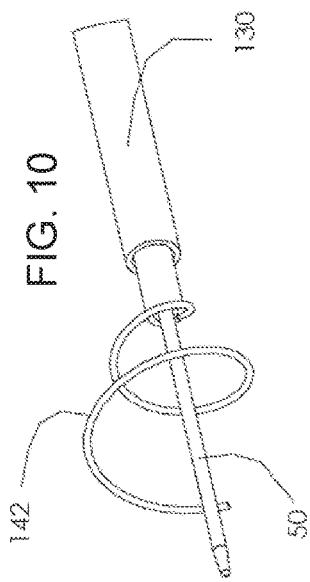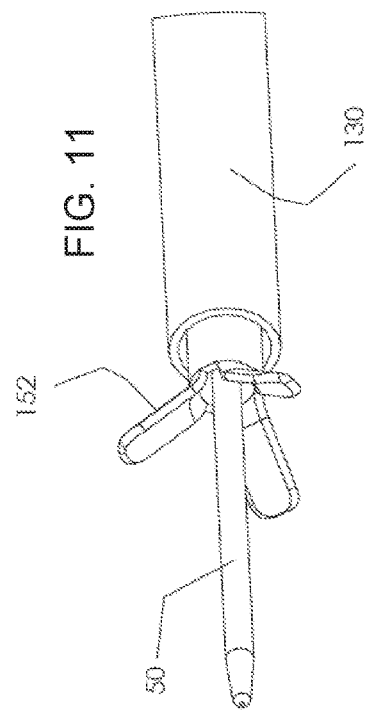

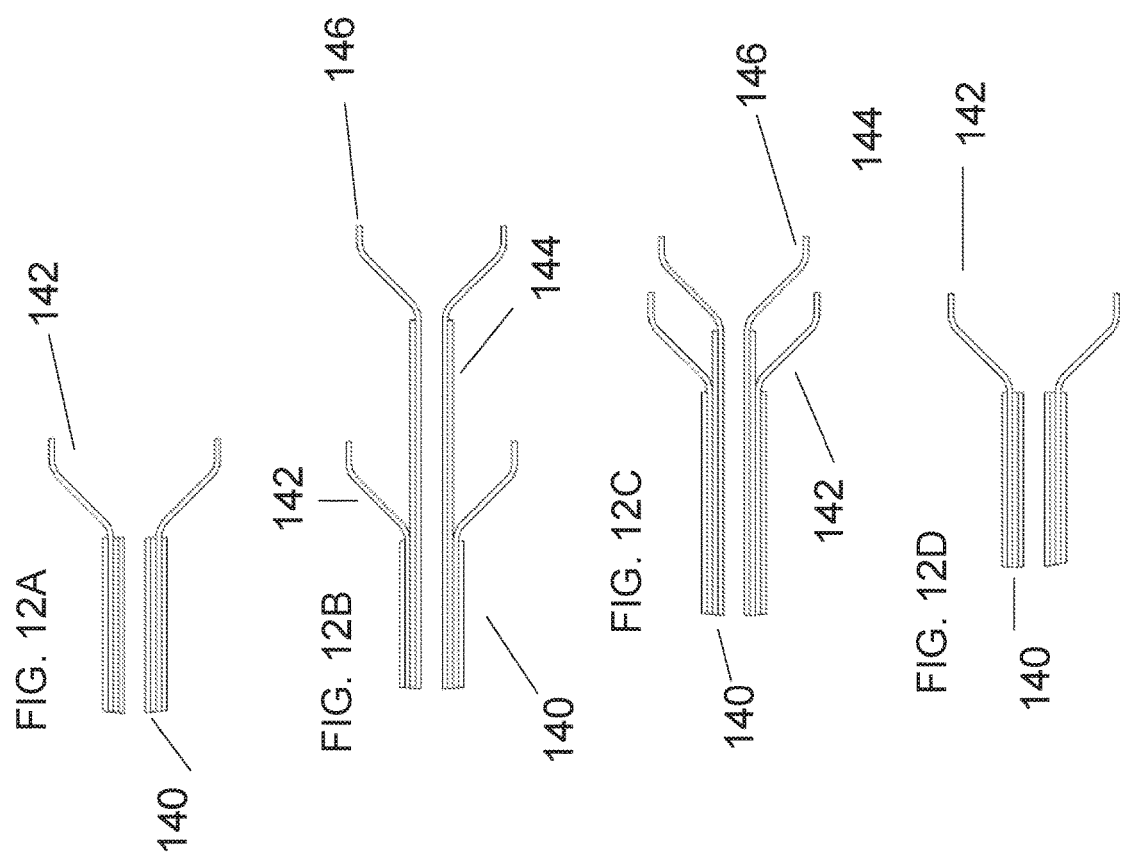

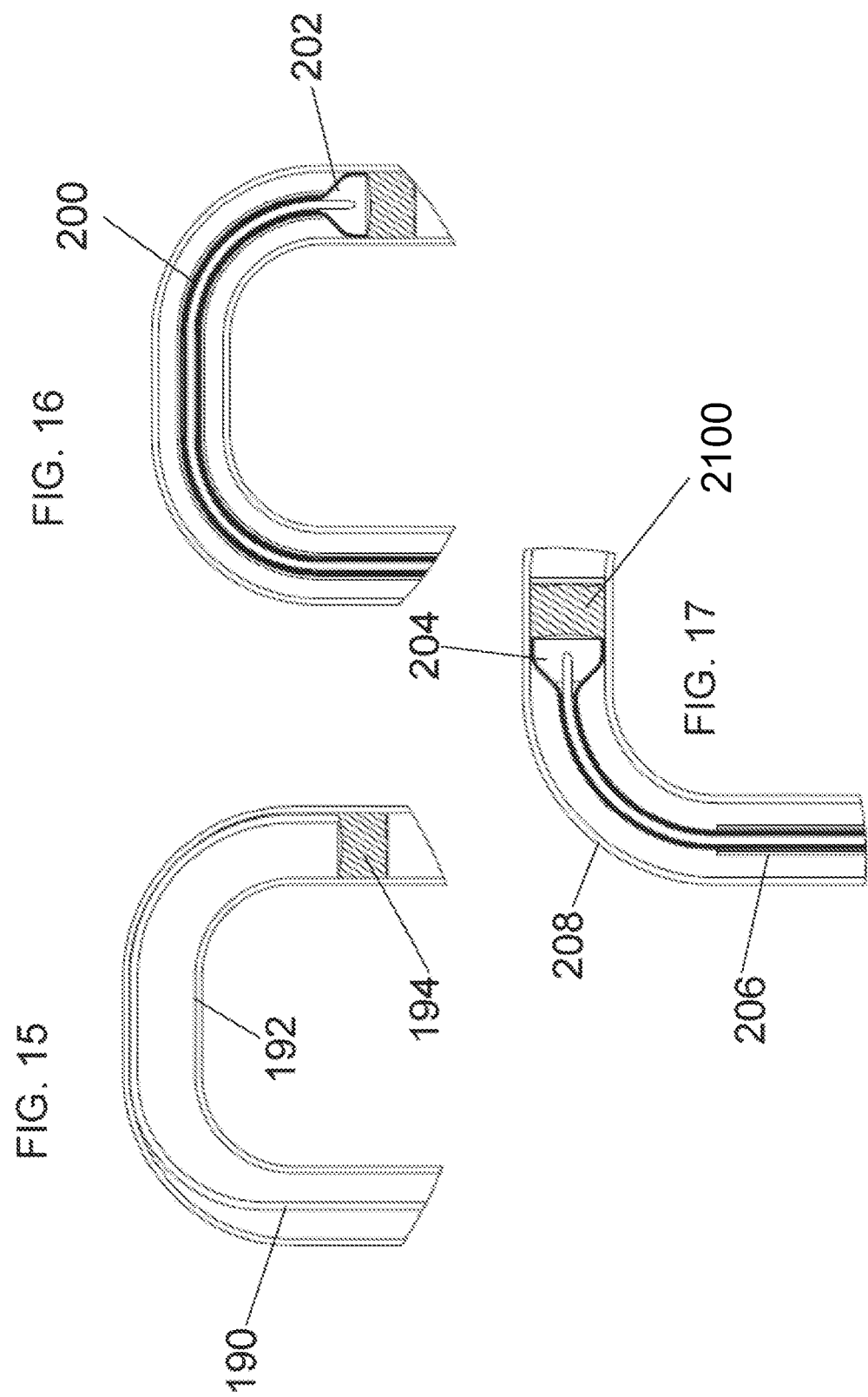

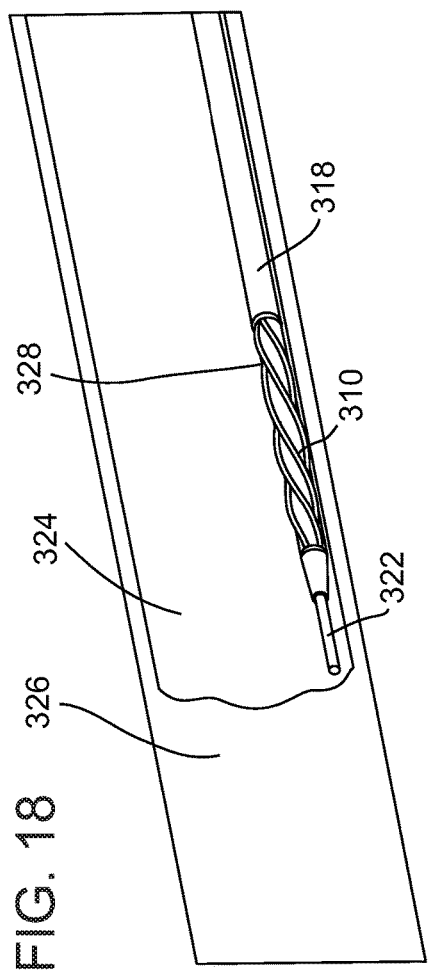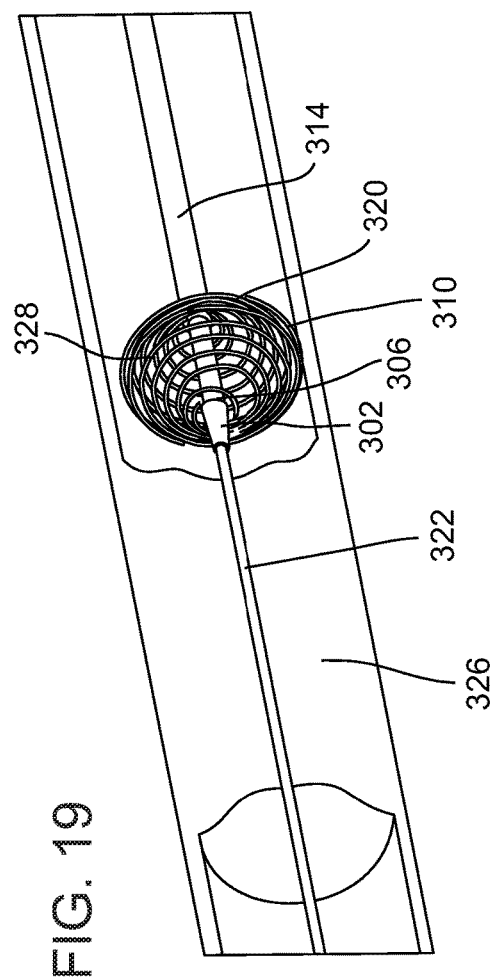

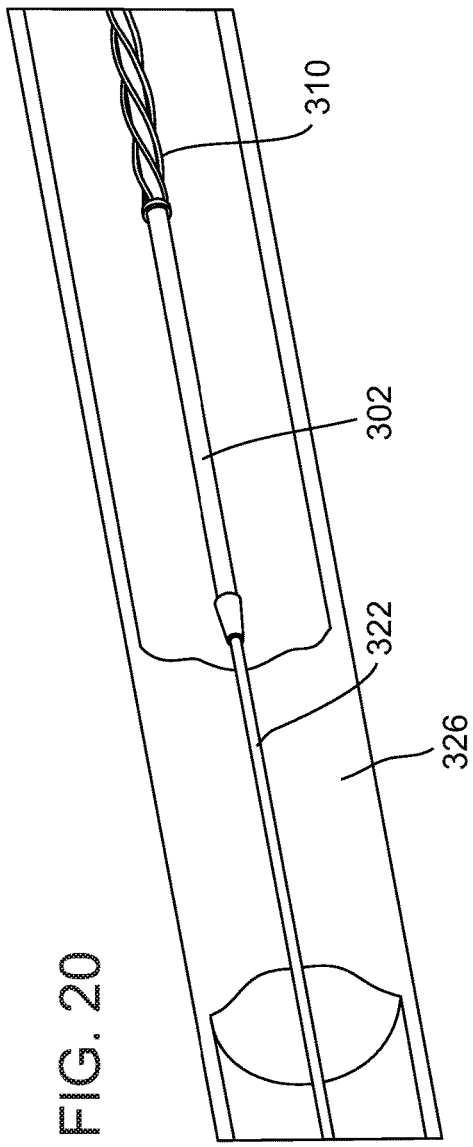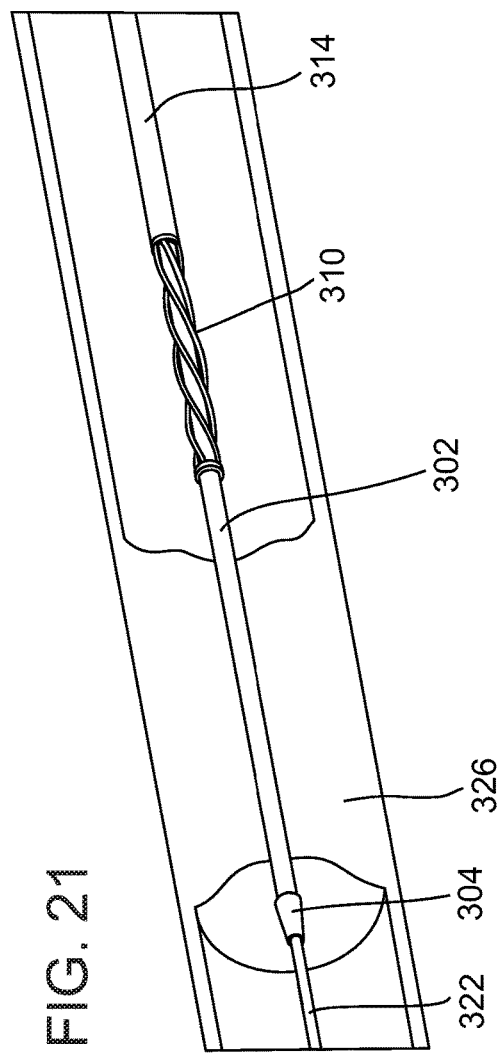

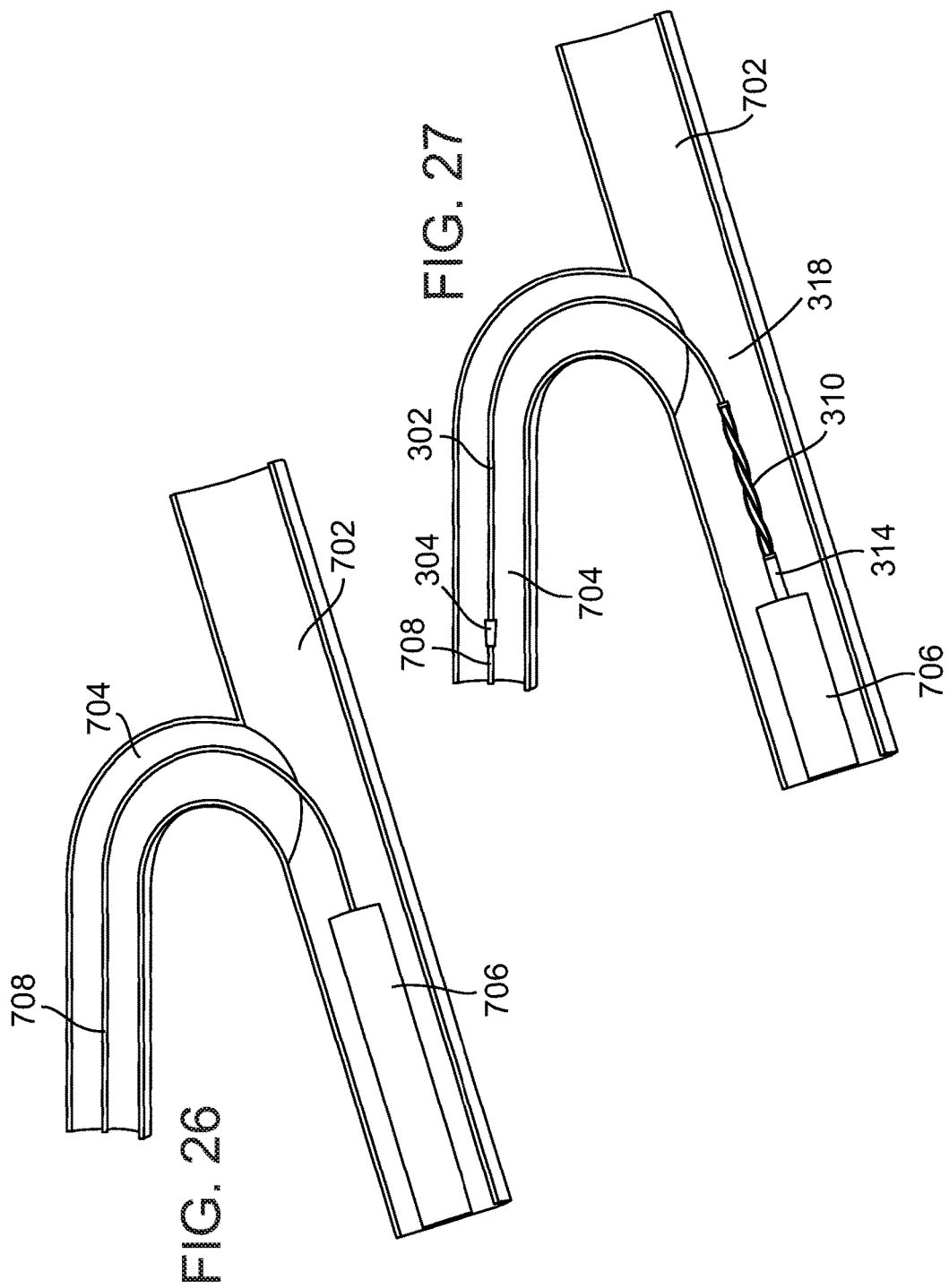

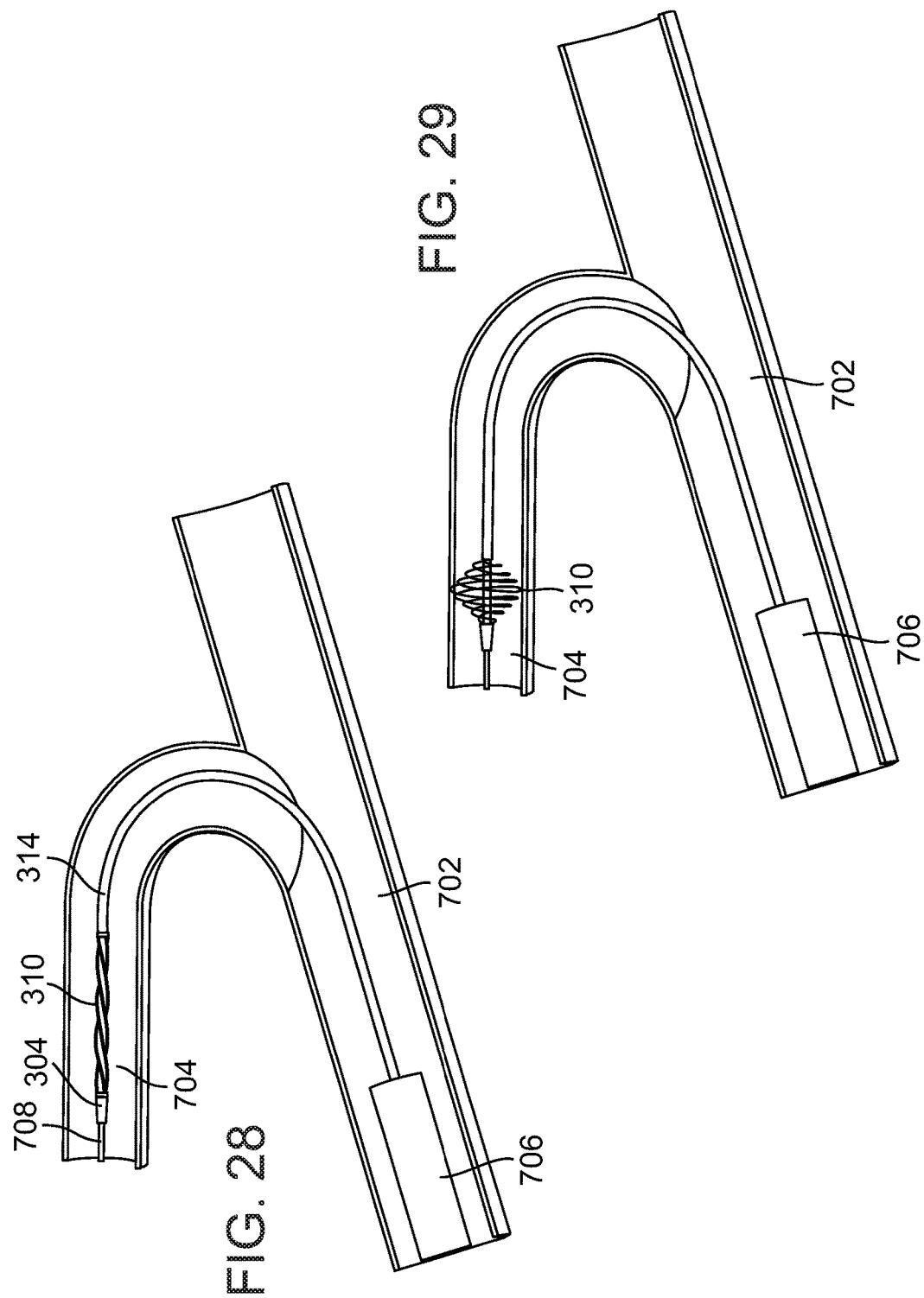

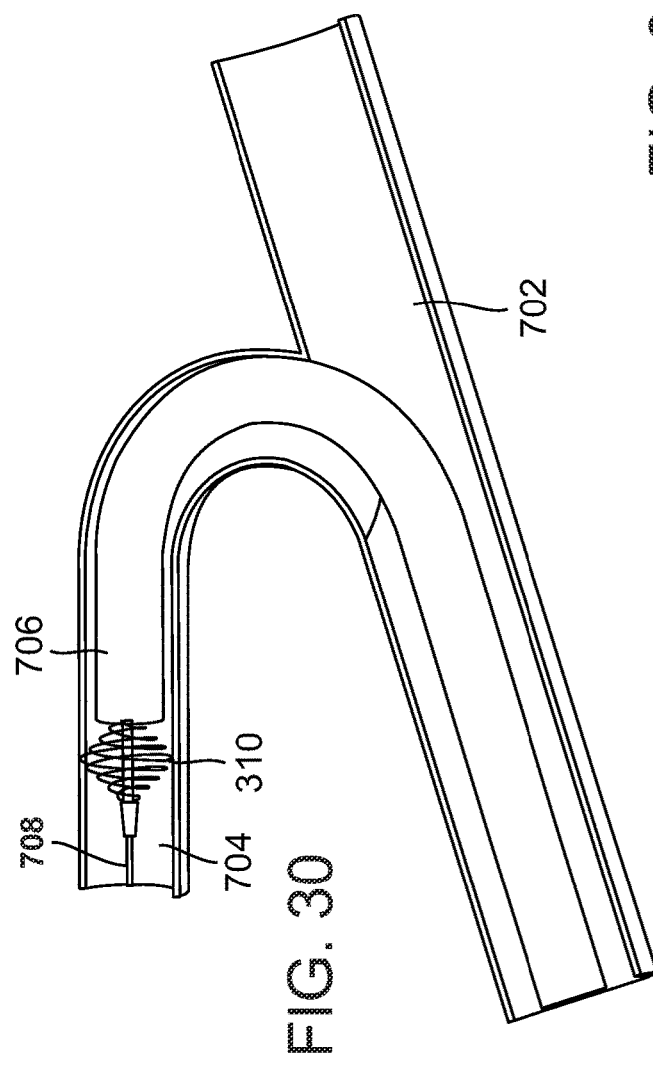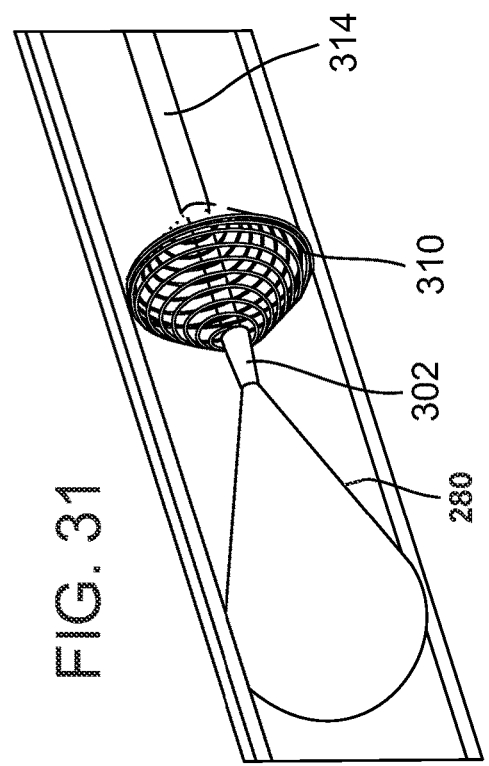

DEPLOYMENT MECHANISM FOR BODY VESSEL INSERTION DEVICES

RELATED APPLICATIONS

This application is a National Phase of PCT Patent Application No. PCT/IL2012/050184 having International filing date of May 23, 2012, which claims the benefit of priority under 35 USC § 119(e) of U.S. Provisional Patent Applications No. 61/488,830 filed May 23, 2011. The contents of the above applications are all incorporated by reference as if fully set forth herein in their entirety.

FIELD AND BACKGROUND OF THE INVENTION

The present invention, in some embodiments thereof, relates to a medical device and/or method for insertion into vessels (e.g., arteries, Eustachian tubes, fallopian tubes), and, more particularly, but not exclusively, to a device and/or method for providing stability and/or support for the distal tip of the device.

Angioplasty is the technique of mechanically widening a narrowed or obstructed blood vessel, typically as a result of atherosclerosis. Angioplasty has come to include all manner of vascular interventions typically performed in a minimally invasive or percutaneous method.

Angioplasty guidewires may be used to guide stent catheters, for example, drug coated stents and/or bioabsorbable scaffolds to keep the vessels open following the procedure and/or to stretch stenoses more open.

In the current art, an empty and collapsed balloon placed at a distal tip of a catheter. The catheter riding on the guide wire, known as a balloon catheter, is passed into the narrowed locations and then the balloon is inflated to a fixed size using water pressures some 75 to 500 times normal blood pressure (6 to 20 atmospheres). The balloon crushes the fatty deposits, opening up the blood vessel for improved flow, and the balloon is then collapsed and withdrawn.

An issue with the current art, is that the blood vessel is often totally occluded and quite seriously misshapen by the obstructions in the blood vessel. Insertion of a leading guidewire (e,g, 0.014" and even thinner distal tip) is a mandatory step required in order to cross an obstructed coronary or peripheral vessel. Guidewire insertion is followed by balloon passage through the atherosclerotic lesion and subsequent dilatation. The guidewire takes a position within the lumen that defines a default/uncontrolled location of the distal tip (e.g. the site of least resistance) but this is not always the center of the lumen and/or the site of vessel occlusion needed for plaque penetration. Thus a balloon or micro-catheter led guidewire fails to be properly centered within the blood vessel.

SUMMARY OF THE INVENTION

According to one aspect of the present invention there is provided a micro-catheter having a deployment element which reversibly elastically expands at the microcatheter tip. Optionally, the deployment element centers the microcatheter tip. Optionally or additionally, the deployment element keeps the microcatheter tip parallel to the vessel wall. Optionally or additionally, the deployment element is adapted to conform to various vessel geometries while still centering the tip.

An aspect of some embodiments of the invention relates to a microcatheter comprising a deployment element disposed about around at least a portion of an exterior of a distal end of the microcatheter, the deployment element configured for repeatedly expanding and collapsing, the distal end arranged to allow forward or reverse axial displacement while the deployment element maintains a position, the deployment element arranged for positioning the microcatheter distal end approximately in the middle of a vessel.

In an exemplary embodiment of the invention, the microcatheter further comprises a first tube sized and shaped for surrounding at least a portion of a guidewire.

In an exemplary embodiment of the invention, the deployment element is disposed around at least a portion of an exterior surface of the first tube so that one or more lumens in the microcatheter are patent.

In an exemplary embodiment of the invention, the microcatheter further comprises: a second tube at least partially disposed around the first tube, the second tube slidingly associated with the first tube, the deployment element arranged relative to the second tube so that relative axial motion between the second tube and the first tube expands or collapses the deployment element.

In an exemplary embodiment of the invention, the deployment element is arranged relative to the second tube so that sliding the second tube axially displaces the deployment element relative to the first tube.

In an exemplary embodiment of the invention, the deployment element comprises a helix.

In an exemplary embodiment of the invention, the first tube comprises a tip shaped for insertion into a lesion.

In an exemplary embodiment of the invention, a ratio of reduction in an axial dimension to expansion in a radial direction of the deployment element is from about 4:1 to 1:4.

In an exemplary embodiment of the invention, a surface of the deployment element is flush with a surface of the second tube.

In an exemplary embodiment of the invention, the deployment element has a cross sectional area in the expanded state that is small enough so as not to block more than 50% of blood flow in the vessel in an amount that cause ischemia to downstream tissues.

In an exemplary embodiment of the invention, the deployment element is arranged to align the microcatheter distal end in parallel with a long axis of the vessel.

In an exemplary embodiment of the invention, at least 3 cm of a distal end of the first tube is made out of a material sufficiently flexible to bend through tortuous vessels.

In an exemplary embodiment of the invention, the microcatheter further comprises a handle adapted to control precise movements of the first tube relative to the second tube.

In an exemplary embodiment of the invention, the deployment element is a long rib that contacts the vessel wall at a small number of contact locations so that the deployment element adjusts to an uneven vessel wall.

In an exemplary embodiment of the invention, the deployment element comprises a resilient structure having at least one outwardly pressing rib to push against a wall of the vessel.

In an exemplary embodiment of the invention, the deployment element is housed within an outer flexible tube in a retracted state and deployed outwardly of the outer flexible tube to attain a predetermined deployed shape, the predetermined deployed shape being attained by resilience within the structure.

In an exemplary embodiment of the invention, the deployment element comprises a tensioned spiral. Alternatively, the deployment element comprises radially opening petals.

In an exemplary embodiment of the invention, the deployment element is angled relative to the distal end in a direction away from a lesion so that the distal end is positioned in near proximity to the lesion in the vessel, the angle is about 15 to about 60 degrees.

In an exemplary embodiment of the invention, the deployment element is arranged to allow the distal end to be positioned within less than about 5 mm from a lesion.

In an exemplary embodiment of the invention, the deployment element is arranged to increase a resistance to reverse motion when the deployment element is deployed in the vessel, by increasing an angle of the deployment element and a surface of the microcatheter.

In an exemplary embodiment of the invention, the deployment element comprises a circumferentially extending helix extending outwardly of a circumference of a guidewire at the distal end, and having distal vertices extending away from the distal end and proximal vertices extending towards the distal end, the deployment element being held to the distal end by secondary ribs connecting the distal end to the proximal vertices.

In an exemplary embodiment of the invention, the microcatheter comprises a second, proximal, deployment element deployable independently of the first, distal deployment element.

In an exemplary embodiment of the invention, the microcatheter has a length and wherein the length of the second tube is flexible.

An aspect of some embodiments of the invention relates to a method of manufacturing a micro-catheter for use in a lumen of a body vessel, the method comprising:

preforming a shaped element for the lumen using a resilient material;

collapsing the shaped element;

inserting the shaped element within a flexible outer tube at a distal end of a micro-catheter inner tube;

inserting a guidewire to extend from the distal end of the inner tube; and providing an extension control to extend the shaped element forward of the micro-catheter to expand into the lumen.

In an exemplary embodiment of the invention, the resilient material comprises an elastic material. Optionally, the elastic material comprises a shape memory material.

Optionally, the shape memory material comprises a material having plateau deformation. Optionally, the shape memory material comprises a nickel titanium alloy including amounts of nickel and titanium which are approximately equal by atomic percentages.

In an exemplary embodiment of the invention, the shaped element comprises a frame. Alternatively, the shaped element comprises a spiral.

In an exemplary embodiment of the invention, the shaped element comprises, when expanded, a helix extending circumferentially about the lumen, the helix having distal vertices and proximal vertices and being connected to the inner tube via bars attached to the proximal vertices.

An aspect of some embodiments of the invention relates to a method of treating a lesion in a blood vessel using a microcatheter having a deployment element on a distal end thereof, the method comprising:

deploying the deployment element in the blood vessel so that the distal end of the microcatheter is secured in the vessel;

piercing a lesion in the lesion with a guidewire advanced through the distal end while the deployment element maintains a position of the distal end; and advancing a tube over the guidewire and into the lesion while the deployment element maintains the position of the distal end.

In an exemplary embodiment of the invention, deploying comprises deploying the deployment element so that the distal end is positioned less than about 10 mm from the lesion.

In an exemplary embodiment of the invention, the method further comprises advancing at least one of the guidewire and the tube through the lesion.

In an exemplary embodiment of the invention, the method further comprises: retracting the deployment element; and advancing the deployment element over the tube into the lesion.

In an exemplary embodiment of the invention, the method further comprises expanding the deployment element in the lesion to increase blood flow through the lesion.

In an exemplary embodiment of the invention, the distal end is deployed approximately in the middle of the vessel.

In an exemplary embodiment of the invention, the distal end is deployed in parallel to walls of the vessel.

An aspect of some embodiments of the invention relates to a method of traversing a tortuous vessel region using a microcatheter having a deployment element thereon, the method comprising:

advancing a distal end of a first microcatheter tube over a guidewire spanning the tortuous region so that the distal end is positioned distally of the tortuous region;

advancing a second microcatheter tube attached to the deployment element at a distal end thereof over the first microcatheter tube, so that the deployment element is positioned distally to the tortuous region;

expanding the deployment element to anchor the second microcatheter tube in a vessel and;

advancing an outer sheath over the second microcatheter tube towards the deployment element thereby traversing the tortuous vessel region.

In an exemplary embodiment of the invention, the method further comprises maintaining a tension of the second microcatheter tube.

In an exemplary embodiment of the invention, the method further comprises alternating the expanding and collapsing of the deployment element to advance within the vessel.

An aspect of some embodiments of the invention relates to a deployment element adapted for use with a distal end of a microcatheter, the deployment element comprising:

one or more outwardly pressing ribs adapted to press against the wall of a vessel, the deployment element configured for repeatedly expanding and collapsing, the deployment element arranged to allow forward or reverse axial displacement of the microcatheter end while the deployment element maintains a position of the microcatheter end, the deployment element arranged for positioning the microcatheter distal end approximately in the middle of a vessel.

In an exemplary embodiment of the invention, the deployment element is further adapted to guide the microcatheter distal end along an axis.

Unless otherwise defined, all technical and scientific terms used herein have the same meaning as commonly understood by one of ordinary skill in the art to which this invention belongs. The materials, methods, and examples provided herein are illustrative only and not intended to be limiting.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified diagram illustrating a first microcatheter internal tube having a retrievable centering 'deployment element' at its distal tip, in accordance with an exemplary embodiment of the invention;

FIG. 2 is an end view that shows the deployment element of the device of FIG. 1 in greater detail;

FIG. 3 is an alternative end view of the deployment element of the device of FIG. 1;

FIG. 4 is a side end view of the deployment element of FIG. 1;

FIG. 5 is a simplified diagram showing an external tube or sleeve for a micro-catheter tube from the distal tip with the deployment element retracted;

FIG. 6 is a simplified diagram showing the micro-catheter inner tube of FIG. 1 inside the external sleeve of FIG. 5 and attached to an operating handle at the proximal end and showing the deployment element in the deployed condition at the distal tip;

FIG. 7 is a simplified diagram showing arrangement of FIG. 6 wherein the operating handle at the proximal end is in a retraction position causing the deployment element to be retracted within the outer tube (not shown) at the distal end, in accordance with some embodiments of the invention;

FIG. 8 is a simplified exploded diagram showing the deployment element in the retracted state within the flexible tube of the micro-catheter tube according to some embodiments of the invention;

FIG. 9 is a simplified diagram showing a guidewire extending from the micro-catheter inner tube, in turn within an outer tube, located within a blood vessel where a deployment element according to an exemplary embodiment is placed at the proximal end to an occlusion site of the microcatheter in the vessel wall;

FIG. 10 is a simplified diagram showing an alternative deployment element according to some embodiments, comprising a spiral rib;

FIG. 11 is a simplified diagram showing a further alternative deployment element according to some embodiments, comprising radially opening petals;

FIGS. 12A to 12D illustrate four successive stages in propelling the micro-catheter tube through a vessel using proximal and distal deployment elements according to some embodiments;

FIG. 15 illustrates a conventional guidewire having a resilient tube length, and shows how the resilience affects the way in which the tube passes through a bend in a vessel;

FIG. 16 illustrates a micro-catheter according to some embodiments, wherein the tube length is flexible but not resilient, and illustrating improved centering of the guidewire over the embodiment of FIG. 15;

FIG. 17 illustrates a variation of the embodiment of FIG. 16 wherein a tube approaches the bend in the vessel and the deployable element's tube extends from the tube to be effectively centered over the bend;

FIG. 18 is a simplified diagram of a microcatheter with an external deployment element inside a vessel, in accordance with an exemplary embodiment of the invention;

FIG. 19 is a simplified diagram of the deployed state of the external deployment device of the microcatheter of FIG. 18;

FIG. 20 is a simplified diagram of the guide wire inserted into the lesion, for example, starting from the microcatheter positioned as in FIG. 19;

FIG. 21 is a simplified diagram of the microcatheter inserted into the lesion, for example, starting from the microcatheter positioned as in FIG. 21;

FIGS. 26, 27, 28, 29 and 30 illustrate a series of steps of using the microcatheter with the external deployment device to navigate through tortuous vessels, in accordance with an exemplary embodiment of the invention;

FIG. 31 is a simplified diagram illustrating injection of materials into the vessel using the microcatheter, in accordance with an exemplary embodiment of the invention;

DESCRIPTION OF THE PREFERRED EMBODIMENTS

Figure 13:
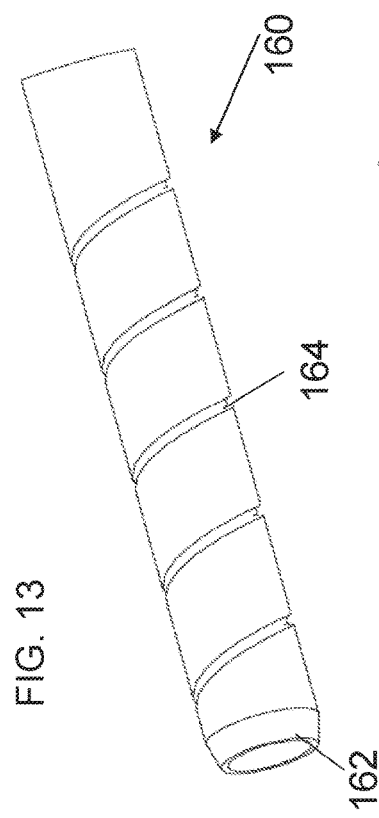
FIG. 13 illustrates an embodiment wherein the microcatheter external tube has a conical end at the distal tip and includes threads.

An aspect of some embodiments of the invention relates to a microcatheter having a deployment element at about the microcatheter tip, the deployment element is arranged to reversibly elastically expand at the microcatheter tip. Optionally, the deployment element is right at the tip, for example, overlapping the tip. Alternatively, the deployment element is distal (e.g., past) the tip. Alternatively, the deployment element is proximal to the tip. For example, using the distal end of the microcatheter as '0' reference, the deployment element is located, for example, at 0 mm, or about +/−1 mm away from the tip (proximally or distally), or about +/−3 mm away, or about +/−5 mm away, or about +/−10 mm away, or about +/−15 mm away, or about +−20 mm away, or about +/−25 mm away, or about +/−30 mm away, or other smaller, intermediate or larger distances away.

In an exemplary embodiment of the invention, the deployment element is arranged to substantially center the distal tip relative to the blood vessel. Optionally, the center is not symmetrical, for example, some deviation to either direction is tolerated. Optionally, the deployment element positions the distal tip within about the central 10% of the blood vessel diameter, or about the central 25% of the vessel diameter, or about 33% of the vessel diameter, or about 50% of the vessel diameter. Alternatively, in some embodiments, the deployment element is arranged to position the distal tip away from the center and towards the vessel wall, for example, to pierce lesions on the vessel wall.

In an exemplary embodiment of the invention, the deployment element is relatively long and arranged into one or more ribs. Optionally or additionally, the deployment element has relatively few contact points with the vessel wall. For example, 2, 3, 4, 6, 8, or other intermediate or larger number of contact points. Potentially, the combination of the long element and the few contact points allow for the deployment element to adjust to an uneven vessel wall surface, while potentially maintaining the centered and/or parallel position of the distal tip.

In an exemplary embodiment of the invention, the deployment element is changed from a collapsed state to an expanded state by relative motion of an outer tube and an inner tube. Optionally, the diameter of the deployment element is no larger than the outer diameter of an outer tube of the microcatheter. Optionally or additionally, the expanded state comprise an expansion outwards (e.g., towards the vessel wall) of the deployment element.

In an exemplary embodiment of the invention, the deployment element is adapted to push against the vessel wall with a force. Optionally, the force provides support for the distal tip of the microcatheter. For example, the distal tip is supported so that a guidewire can be pushed through a lumen in the microcatheter. Optionally, the force applied is enough to maintain the position of the distal tip while allowing insertion of the guidewire into an occlusion in the vessel. Not necessarily limiting examples of occlusions include plaques (e.g., extending inwardly from the vessel wall), emboli (e.g., originating upstream that got stuck in the vessel), thrombus (e.g., clots formed inside the vessel lumen). Optionally or additionally, the applied force is not strong enough to damage the vessel wall.

In an exemplary embodiment of the invention, the deployment element stabilizes the distal tip of the microcatheter. Optionally, the distal tip of the microcatheter is stabilized when the guidewire and/or catheter tube is pushed through the lumen of the microcatheter. Optionally or additionally, the distal tip of the microcatheter is stabilized as the microcatheter tube and/or guidewire are pushed into the lesion in the blood vessel.

In an exemplary embodiment of the invention, the deployment element is disposed so that one or more lumens of the microcatheter are patent. Optionally, the deployment element is disposed at least partially along the outer circumference of the microcatheter.

In an exemplary embodiment of the invention, the deployment element is arranged to position and/or maintain the microcatheter tip parallel to the vessel wall.

In an exemplary embodiment of the invention, the deployment element is reversibly moved between the collapsed and expanded states multiple times. For example, when advancing through blood vessels.

In an exemplary embodiment of the invention, the deployment element comprises one or more resilient members in a resilient elastic structure that uses the resilience to press outwardly against the vessel walls.

In an exemplary embodiment of the invention, the micro catheter comprises two tubes, an internal tube housing the guidewire, and an external tube for sliding through the blood vessel. Optionally, the outer tube is flexible. In an exemplary embodiment of the invention, a deployable element extends outwardly from the distal end of the microcatheter as will be explained. Optionally, a handle is placed at the proximal end of the guidewire for user control, for example, to deploy the deployable element.

In an exemplary embodiment of the invention, the shaping of the structure allows for even pressure in all directions of the vessel. The structure may be made of a shape memory material that can be shaped for the specific vessel prior to deployment, for example, for the coronary arteries, for the small vessels of the brain. The shape memory material may have a plateau deformation property. The material used may be a nickel titanium alloy such as nitinol. Nitinol is characterized by shape memory and superelasticity, and the nickel and titanium are present in roughly equal atomic percentages.

An aspect of some embodiments of the invention relates to a microcatheter with a deployment element on the microcatheter, the deployment element not being located within a lumen of the microcatheter. In an exemplary embodiment of the invention, the deployment element is sized and/or positioned to secure the microcatheter approximately in the middle of the vessel (e.g., blood vessel).

In an exemplary embodiment of the invention, the deployment element is exteriorly located relative to the lumens of the inner and/or outer tubes. Optionally, the deployment element is disposed along the outer surface of the microcatheter. Potentially, the lumens are free for other uses, for example, for insertion of guidewires, fluid delivery.

In an exemplary embodiment of the invention, at least a portion of the microcatheter tip can be displaced relative to the deployed deployment element, the displacement occurring while the deployment element maintains the position of a distal end of the microcatheter. Optionally, the inner tube of the microcatheter is displaced, for example, proximally and/or distally in an axial direction.

In an exemplary embodiment of the invention, the deployment element is deployed or retracted by lateral displacement of an inner tube relative to an outer tube. Optionally, the axial length change between the tubes is translated into changes in radial diameter of the deployment element. Optionally or additionally, the relative positions between the inner and outer tubes are lockable, for example, by a handle.

In an exemplary embodiment of the invention, the expansion in radial diameter is by a factor of about 2×, about 3×, about 4×, about 5×, about 6×, about 7×, about 8×, or other smaller, intermediate or larger expansion ratios. For example, in the compressed state, the outer diameter of the deployment element can be about 1 mm, and the outer diameter in the deployed state can be about 6 mm.

In an exemplary embodiment of the invention, the deployment element is located proximally to the tip of the microcatheter and does not deploy past the catheter tip. Alternative or additionally, the deployment element is angled in a proximal direction (e.g., away from the tip). Potentially, the location of the deployment element in the collapsed and/or expanded states allowed the microcatheter to be placed in close proximity to a lesion in the blood vessel.

An aspect of some embodiments of the invention relates to a method of traversing blood vessels using the microcatheter having the exteriorly located deployment device. Optionally, the vessels are tortuous, for example, the method allows passing through branch vessels having an angle (measured from the axis of the microcatheter distal end when moving forward) of, for example, greater than about 90 degrees, or greater than about 120 degrees, or greater than about 150 degrees, or other smaller, intermediate or larger angles. Not necessarily limiting examples of tortuous blood vessels include; coronary arteries, small arteries of the brain. Not necessarily limiting examples of the turning radius possible using the method include; about 1 mm, about 2 mm, about 3 mm, about 4 mm, about 5 mm, or other smaller, intermediate or larger values.

In an exemplary embodiment, the method comprises advancing the microcatheter having the deployment element at the distal end thereof across the torous anatomy. Optionally, the inner tube is advanced over a guidewire and across the tight turn. Optionally or additionally, the outer tube is advanced over the guidewire and around the tight vessel junction.

In an exemplary embodiment of the invention, the method further comprises deploying the deployment element to secure the distal end of the microcatheter distally to the difficult anatomical location. For example, by relative motion of the inner and outer catheters.

In an exemplary embodiment of the invention, the method further comprises advancing an outer sheath over the microcatheter and across the tortuous anatomy. Potentially, the outer sheath is passable around the tight turn due to the secured distal position of the microcatheter.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Exemplary Deployment Device

Reference is now made to FIG. 1, which is a simplified schematic diagram showing a flexible micro-catheter 110 which consists of two main elements: a substantially elongate inner tube 112 and a distal deploying element 114, in accordance with an exemplary embodiment of the invention. Optionally, the deploying element 114 is a resilient frame and/or a pre-shaped element in general which is preformed to frame a body lumen that it is intended to be used with. Optionally, these two elements are rigidly connected from two parts. Alternatively may be produced as an integrated single component. For example a laser may be used to cut around the tip of a nitinol tube to form the deployment element. A heat treatment process may be used to shape the tip to set it in its deployed state.

In an exemplary embodiment of the invention, the distal deploying element is made of a super-elastic material with shape memory, and/or a super-elastic material having a plateau deformation property, for example, Nitinol. In an exemplary embodiment of the invention, the shape memory is used to allow fold down of the deployment element after use.

In an exemplary embodiment of the invention, the tube and/or deployment element are placed and surround a guide wire, for example, the distal tip of the guidewire.

In an exemplary embodiment of the invention, the flexible micro-catheter 110 is used for passing through a vessel and/or for penetrating occlusions. The deployment element 114, at the distal tip, may lead and support the guidewire while passing through the vessel, and enable the guidewire to pass occlusions, for example, occlusions that extend inwardly from the wall of the vessel, or occlusions that formed elsewhere and got trapped in the vessel.

In an exemplary embodiment of the invention, the deployment element has a structure in which one or more outwardly pressing ribs extend against the wall of the vessel. The rib or ribs are shaped as will be discussed in greater detail below, to apply pressure around the walls of the vessel. Optionally, even pressure is applied to the walls. In some embodiments, the ribs are part of a loop design or a helix, or the like.

FIG. 2 is a simplified schematic diagram of an embodiment of deployment element 114, in accordance with some embodiments of the invention. FIG. 3 and FIG. 4 are side and front schematic views of the deployment element 114 of FIG. 2. As shown, in some embodiments, the deployment element consists of three bars 116 which are connected with struts 118 arranged as a circumferential loop. The result is a blunt loop/circular like geometry which is therefore not harmful or traumatic for the vessel. In some embodiments, the round shape both presses evenly on the walls of the vessels and/or holds the guidewire rigidly at its center. More or less than three of the connecting bars 116 may be used in embodiments, for example, 2, 4, 6, or other smaller, intermediate or larger numbers. Optionally, struts 118 are a single continuous rib formed into a loop around the circumference of the guidewire at the radius of the vessel. Optionally, the bars hold the vertices of the loop that are proximal to the guidewire.

A potential advantage of the design of FIG. 2, is that the design permits a relatively short element that still has a substantial deployment ratio, and thus can be positioned near the occlusion.

FIG. 5 is a simplified schematic diagram which shows an external tube 130, in accordance with some embodiments of the invention. In FIG. 5 the external tube is shown alone. As further detailed in FIGS. 6 & 7, the external tube is assembled over inner flexible tube 110 carrying deployment element 114. The external tube 130 is preferably made of conventional medical catheter materials, not necessarily limiting examples include; PTFE, PET, Polyurethane, Polypropylene, Polyamide, Polyethylene, Silicone, and may include reinforcing elements such as metallic coils, and/or radio-opaque elements such as gold/tungsten markers, barium-sulfate particles.

FIG. 6 is a simplified schematic diagram which shows the centralizing device in its deployed configuration in which the inner tube and guidewire are inside the outer tube and the deployment tip is deployed externally at the distal end, in accordance with some embodiments of the invention.

In some embodiments, the device is operated at its proximal end by forward driving button 134, which is rigidly connected to flexible inner tube 110, relative to handle 132. In some embodiments, handle 132 is rigidly connected to external tube 130, so that forward movement of button 134 pushes forward the inner tube in relation to the outer tube and deploys the deployment element 114.

In some embodiments, when button 134 is retained backwards, as shown in FIG. 7, inner tube 110 does not extend outwardly of the distal end of the outer tube and deployment element 114 (not shown) is collapsed and held within external tube 130.

FIG. 8 is a simplified schematic exploded diagram which shows deployment element 114 at its constrained collapsed configuration, in accordance with some embodiments of the invention.

In some embodiments, elastic deformations of deployment element 114 occur in between its deployed configuration as shown in FIG. 2 and its constrained configuration as shown in FIG. 8.

In an exemplary embodiment of the invention, distal element 114 is optimized in the sense that its critical points are designed to utilize the maximal elastically properties of a shape memory material such as Nitinol, potentially enabling a maximal deployment ratio, with minimal longitudinal dimensions, and maximal deployment force.

Without being bound to theory, the above-mentioned optimization is based on a formula which calculates the maximal strain (epsilon) in between an unconstrained and a constrained geometry having radii of curvature R1 and R2 respectively. Even if the theory is incorrect, this does not preclude some embodiments of the invention from working as described.

$$\text{Epsilon} = -H \times [(R1/R2) - 1] / [(2 \times R1) - h]$$

wherein, "H" is the height of the strut along its longitudinal (bending) dimension.

Referring again to FIG. 2 the element 114 may be considered in segments A, B, C and D having radii of curvatures: R1a, R1b, R1c, R1d, respectively. The same element is shown in FIG. 8 in the constrained geometry having radii of curvatures: R2a, R2b, R2c=∞, R2d=∞, respectively. When calculating critical segments A, B, C & D within the distal element's 114 unconstrained geometry as per FIG. 2 and constrained geometry as per FIG. 8, and given heights of Ha, Hb, Hc & Hd respectively, the use of elastic elements to form the structure of deployable element 114 becomes optimal over merely tensioned elements as the critical segments may have an 8% strain. Such a strain is normally considered as the maximal elastic strain of a Nitinol or like shape memory substance.

Optionally, deployable element 114 has thin bars 116 which have small Hc and Hd dimensions, relative to the loop's width, that is the Ha & Hb dimensions. In such a case of thin bars the deployment force is determined by the nature of the loop. Moreover, when the loop is made of Nitinol and is designed for elastic deployment having 2%-6% strains—using the formula specified above—then the loop is able to centerline the guide wire even if it is deployed inside a non-circular (pathological) tissue, such as an artery, with a plaque that renders it non-circular. Without being bound to theory, this phenomena occurs due to the plateau property of the Nitinol which applies substantially the same forces over the range of 2%-6% strain. The plateau property potentially enables the loop to adapt itself to the shape of a vessel wall independently of the level of the irregular geometry of the wall. A potential advantage is that the guidewire is directed by averaging the lumen's (pathological) geometry.

FIG. 9 is a simplified schematic diagram which shows how the device directs guide wire 50 towards the center occlusion 80 which blocks or dramatically reduces the blood flow inside vessel 60, in accordance with an exemplary embodiment of the invention.

As mentioned, in some embodiments, the device tip is made of Nitinol, which is substantially elastically deformed with a relatively constant force, as per the plateau property of Nitinol discussed above. Thus, the device tip boundaries in effect sense and adjust themselves to the vessel pathological morphology, which may be substantially irregular, and thus automatically direct guide wire 50 towards the center of the lumen of the vessel 60.

In contrast, a balloon, which centralizes the guide wire by reconstructing the vessel, may not direct the guide wire towards the vessel lumen's true center. Both the centralizing property as described hereinabove, which is independent of the vessel's morphology, and the device's loop like blunt design dramatically reduce the risk of perforating the vessel's wall. The device of the present embodiments also enables the user (e.g., surgeon, interventional cardiologist, interventional radiologist) to apply larger forces to pass guide wire 50 through occlusion 80. The vector of the force may be more accurately along the center line as well.

Exemplary Microcatheter with Exterior Deployment Device

Figure 34A:
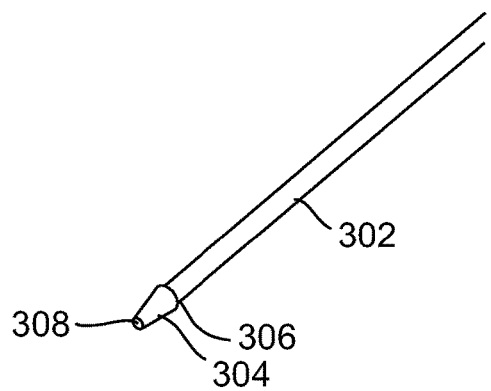
FIGS. 34A to 34C are simplified diagrams of components of a microcatheter with the external deployment element, in accordance with an exemplary embodiment of the invention.
Figure 34B:
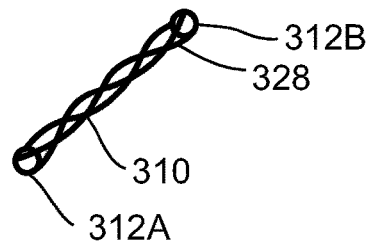
Figure 34C:
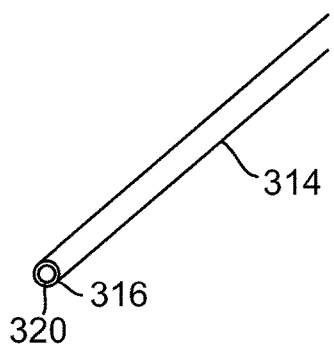
Figure 34D:
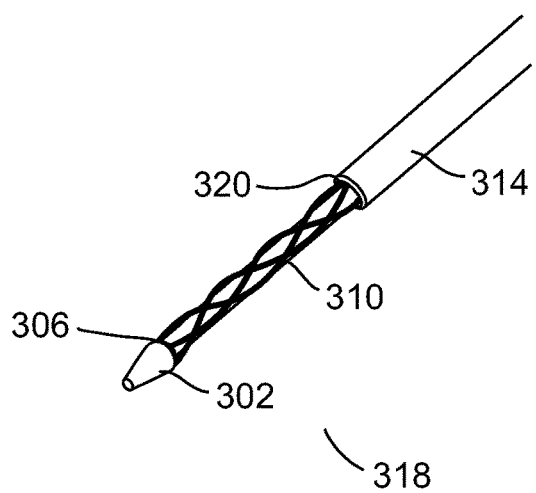
FIG. 34D is the assembled microcatheter with the external deployment element using elements of FIGS. 34A-34C.

FIGS. 34A-C are simplified drawings of elements of the microcatheter with an exterior positioned deployment element, in accordance with an exemplary embodiment of the invention. FIG. 34D is an assembled microcatheter 318 using the components of FIGS. 34A-C, in accordance with an exemplary embodiment of the invention.

In an exemplary embodiment of the invention, microcatheter 318 comprises an inner tube 302, an outer tube 314, and a deployment element 310. In an exemplary embodiment of the invention, axial displacement of inner tube 302 relative to outer tube 314 deploys deployment element 310.

In an exemplary embodiment of the invention, inner tube 302 comprises a distal tip 304. Optionally, tip 304 is shaped for piercing of a lesion (e.g., thrombus, embolus, plaque, atheroma), for example, by being tapered and/or conical.

Optionally, tip 304 is shaped to be flush against a guidewire extending out through lumen 308 (e.g., without a gap between the guidewire and tip 304).

In an exemplary embodiment, tip 304 forms a flange 306 around at least a portion of the exterior circumference of tube 302. Alternatively, flange 306 is a separate element from tip 304 (e.g., tip is flush with tube 302). Alternatively, there is no flange 306 (e.g., tip is flush with tube 302).

In an exemplary embodiment of the invention, inner tube 302 comprises a lumen 308 sized for accepting a guidewire. The caliber of the guidewire is, for example, about 0.2 mm, about 0.25 mm, about 0.3 mm, about 0.35 mm, about 0.4 mm, about 0.5 mm, or other smaller, intermediate or larger diameters. Optionally, there is more than one lumen, for example, a second lumen for injection of contrast.

In an exemplary embodiment of the invention, outer tube 314 comprises a lumen 316 sized for insertion of inner tube 302 therein.

In an exemplary embodiment of the invention, an external diameter of outer tube 314 forms a flange 320 relative to the surface of inner tube 302 (e.g., when inner tube 302 is inserted in lumen 320).

In an exemplary embodiment of the invention, axial displacement of inner tube 302 relative to outer tube 314 increases or decreases the distance between flanges 306 and 316. Optionally, inner tube 302 is moved and outer tube 314 remains stationary. Alternatively, outer tube 314 is moved and inner tube 302 remains stationary. Alternatively, both inner tube 302 and outer tube 314 are moved.

In an exemplary embodiment of the invention, inner tube 302 and/or outer tube 314 are produced from available materials, not necessarily limiting examples include; nylon, polyimide, polyamide, PTFE, metals (e.g., metallic multi helix tubes) and/or combinations of polymers with metallic reinforcement (e.g., polymer made tube having metallic braining wire reinforcement therein, metallic multi-helix tubes having a polymeric coating thereof. Optionally, inner tube 302 and/or outer tube 314 are coated with a hydrophilic coating (e.g., hydrophilic polysaccharide), for example, to enable low friction of the device against the vessel walls. Potentially, the low friction reduces or prevents trauma to the vessel wall.

In some embodiments, the distal portion of inner tube 302 and/or outer tube 314 are made from a relatively more flexible material than the rest of the catheter, for example, the most distal 10 mm, or 20 mm, or 30 mm, or 50 mm, or other smaller, intermediate or larger sizes. Potentially, the flexible distal tip provides for navigation through tight turns in the blood vessels, for example, as described herein.

In an exemplary embodiment of the invention, a deployment element, for example, helix 310 (e.g., one or more helixes can be used) is disposed along the outer surface of inner tube 302, between flange 306 and flange 320. Optionally, helix 310 comprises reinforced edges 312 (e.g., proximal and/or distal) for positioning against flanges 306 and/or 320. Optionally, helix 310 is flush with the surface of outer tube 314 and/or at least some of distal tip 304.

In an exemplary embodiment of the invention, helix 310 is secured to outer tube 314 (e.g., at flange 320), for example, by glue, friction, crimping or other methods. Optionally, helix 310 is not secured to inner tube 302, for example, able to slide over the exterior of tube 302. Alternatively, helix 310 is attached to inner tube 302 and to outer tube 314. Alternatively, helix 310 is attached to inner tube 302 but not to outer tube 314. Alternatively, helix 310 is not attached to either inner tube 302 or outer tube 314, for example prevented by sliding off tube 302 by flanges 306 and/or 320.

A potential advantage of the externally positioned deployment element is freeing up the inner lumens of the tubes. Another potential advantage is that the outer diameter of the microcatheter is not larger with the deployment element than without the deployment element (e.g., when deployment element is not deployed). Potentially, the presence of the helix (or other deployment element on the catheter) does not interfere with passing the microcatheter through the vascular.

Exemplary Method of Operation

Figure 39:
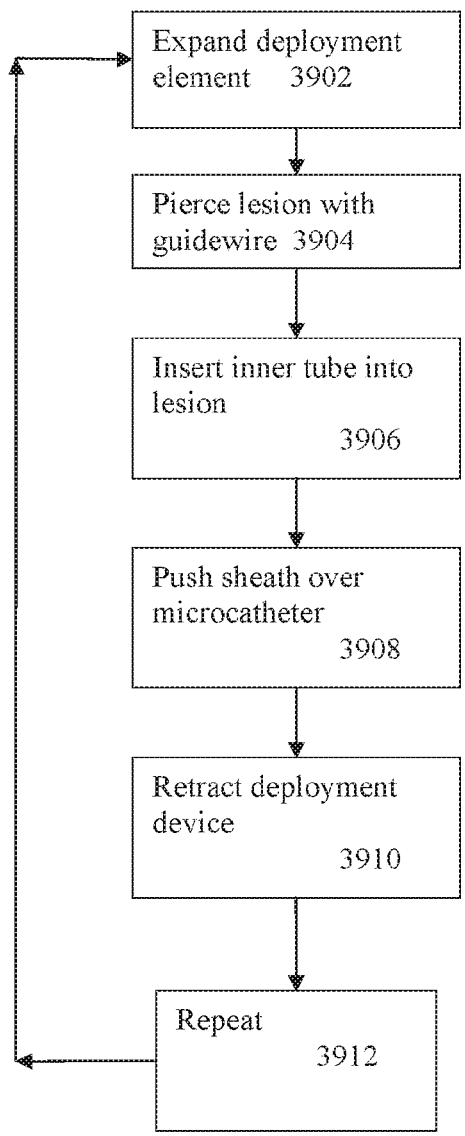
FIG. 39 is a method of operation using the microcatheter with deployment device, in accordance with an exemplary embodiment of the invention.

FIG. 39 is an exemplary method of operation using the deployment element at the tip of the microcatheter, in accordance with an exemplary embodiment of the invention. The method is not meant to be necessarily limiting, as some boxes are optional and some boxes can be repeated in different orders. Furthermore, different deployment elements can be used.

At 3902, the deployment element is expanded to secure the position of the distal end of the microcatheter in the vessel, in accordance with an exemplary embodiment of the invention. Optionally, the deployment element is expanded by relative motion of the inner and outer tubes, for example, as described with reference to FIGS. 35A-C (e.g., using the handle). Alternatively, the deployment element is expanded by retraction of an outer encasing sheath, for example, as described with reference to FIG. 6.

In an exemplary embodiment of the invention, the deployment element is expanded when inside a vessel in near proximity to a lesion, for example, as described with reference to FIG. 18.

Optionally, at 3904, the guidewire is pushed into the lesion, in accordance with an exemplary embodiment of the invention. In an exemplary embodiment of the invention, the deployment element secures the position of the end of the microcatheter as the guidewire is being pushed into the lesion. Optionally, the guidewire is pushed parallel to the vessel wall, the parallel position provided by the deployment element. Optionally or additionally, the guidewire is pushed into the central part of the lesion, the piercing position provided by the deployment element.

Further details of piercing the lesion with the guidewire are provided, for example, with reference to FIG. 19.

Optionally, at 3906, the inner tube of the microcatheter is pushed into the lesions, in accordance with an exemplary embodiment of the invention. Optionally, as in 3904, the deployment element provides one or more functions during the piercing, for example, stability, centering and/or parallel positioning.

Optionally, the outer tube is retracted before pushing the inner tube, for example, as described with reference to FIG. 20.

Further details of piercing the lesion with the inner tube are provided, for example, with reference to FIG. 21.

Optionally, at 3908, an outer encasing sheath is pushed over the proximal end of the microcatheter towards the distal end. Optionally, the sheath is pushed across tight turns in the vessels. Further details of pushing the sheath over the guidewire are provided, for example, with reference to FIG. 30.

At 3910, the deployment element is retracted, in accordance with an exemplary embodiment of the invention. Optionally, retraction of the element is performed by relatively motion of the inner and outer tube. Alternatively of additionally, retraction is performed by encasing the deployment element in a sheath.

Optionally, at 3912, one or more of 3902, 3904, 3906, 3908, 3910 are repeated.

In some embodiments, 3902 and 3910 are repeatable, for example, the deployment element can be expanded and retracted repeatedly.

In some embodiments, the method is used to pierce through a lesion, for example, using 3902, 3904, optionally using 3906 and 3910. The method can be repeated (3912) to pierce through other lesions.

In some embodiments, the method is used to pass a catheter through tortuous blood vessels, for example, using 3902, 3908, 3910 and repeating (3912) as necessary to pass all the tight turns to reach the target tissue.

Exemplary Microcatheter with Deployment Device

FIG. 18 is a diagram of microcatheter 318 inside vessel 324 having a vessel blocking lesion 326 (e.g., thrombus, embolus, plaque), in accordance with an exemplary embodiment of the invention. In an exemplary embodiment, microcatheter 318 has been threaded over a guidewire 322.

In an exemplary embodiment of the invention, helix 310 is located proximally to a distal tip of catheter 318, for example, about 1 mm away, about 3 mm away, about 5 mm away, about 10 mm way, or other smaller, intermediate or larger distances. A potential advantage of the proximal location of the deployment element is that guidewire 322 can be positioned close to lesion 326, for example, without interference from the deployment element.

FIG. 19 is a diagram of microcatheter 318 with the deployment element (e.g. helix 310) having been deployed, in accordance with an exemplary embodiment of the invention.

In an exemplary embodiment of the invention, helix 310 has been compressed and/or deformed by reducing the axial distance between flange 306 of inner tube 302 and flange 320 of outer tube 314. Helix 310 is biased and/or shaped so that reduction in the axial length is translated into expansion and/or an increase in the radial dimension.

In an exemplary embodiment of the invention, the ratio of compression of helix 310 in an axial direction to the corresponding expansion in the radial direction is, for example, about 1:1, or about 1.5:1, or about 2:1, or about 3:1, or about 4:1, or about 5:1, or about 6:1, or about 7:1, or about 1:1.5, or about 1:2, or about 1:3, or about 1:4, or about 1:5, or about 1:6, or about 1:7, or other smaller, intermediate or larger ratios are used.

In an exemplary embodiment of the invention, microcatheter 318 (e.g., deployed helix 310) provides distal support to guidewire 322. Optionally, the support allows for pushing of guidewire 322 inside lesion 326 (e.g., by an operator from outside the body). Potentially, the risk of guidewire 322 moving and perforating the vessel wall is reduced or prevented. Potentially, the risk of guidewire 322 inserted into lesion 326 at an angle, with a projection towards the vessel wall, is reduced or prevented.

Figure 22:
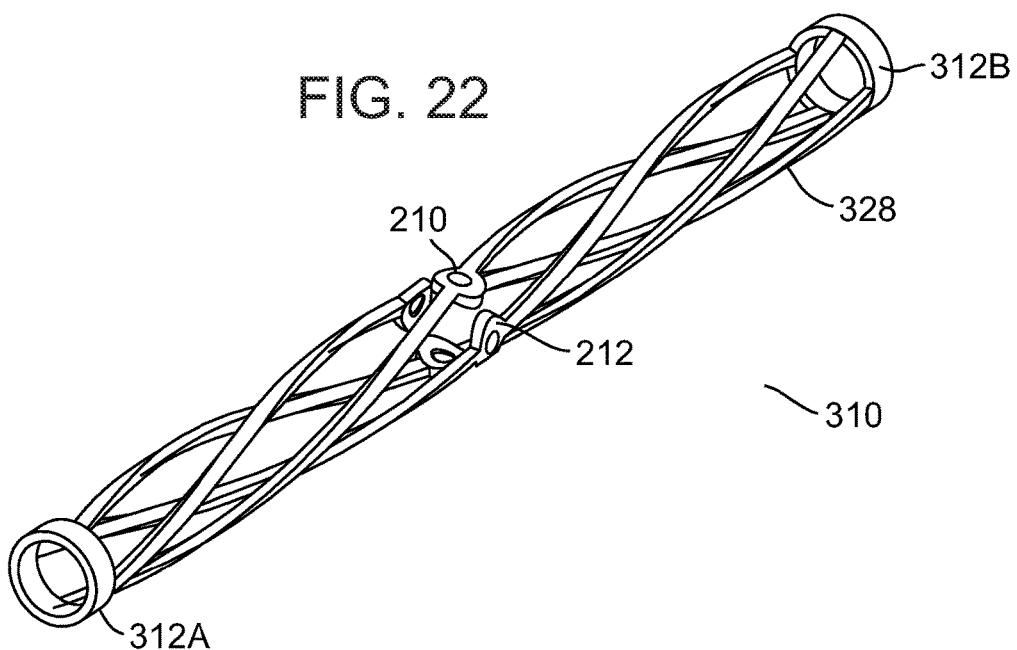
FIG. 22 is a simplified diagram of the external deployment device used with the microcatheter of FIG. 18.

FIG. 22 is blown up picture of helix 310. In an exemplary embodiment of the invention, helix 310 is made up of a shape memory metal, for example, Nitinol.

Optionally, one or more radio-opaque markers 210 and/or 212 are positioned within helix 310. Some not necessarily limiting examples of radio-opaque markers include; gold, tungsten, platinum. (e.g., within struts 328). Optionally, markers 210 and/or 212 are placed within struts 328, for example, inside a pre-cut hole, for example, by using a laser to melt the front and back edges to a bigger caliber so that the markers are geometrically locked inside the hold. Optionally, markers 210 and/or 212 are embedded within struts 328 at the location which will experience the larger deformation, for example, approximately the middle of struts 328. Potentially, markers 210 and/or 212 are used to help estimate the radial expansion diameter of helix 310.

In an exemplary embodiment of the invention, deployed helix 310 is sized and/or shaped to approximately center microcatheter 318 inside vessel 324, for example, helix 310 expands approximately equally around the circumference of microcatheter 318. In an exemplary embodiment of the invention, helix 310 expands to a total diameter of about 1 mm, or about 2 mm, or about 3 mm, or about 4 mm, or about 5 mm, or other smaller, intermediate or larger diameters.

In an exemplary embodiment of the invention, helix 310 comprises at least one strut 328 compressible in an axial direction, for example, 2, 4, 8, or other intermediate or larger numbers of struts are used. Optionally, struts 328 are arranged approximately equally spaced apart around the circumference of inner tube 302. Optionally, struts 328 have a relatively long pitch, for example, one tip of strut relative to another completes no more than about 30 degree (e.g., turn relative to circumferential surface of inner tube 302), or no more than about 60 degrees, or 90 degrees, or 180 degrees (e.g., half a turn), or 270 degrees, or 1 turn, or 2 turns, or 4 turns, or other smaller, intermediate or larger number of turns. In an exemplary embodiment of the invention, the axial length of helix 310 is, for example, about 10 mm, or about 20 mm, or about 30 mm, or about 40 mm, or about 50 mm, or other smaller, intermediate or larger sizes.

In an exemplary embodiment of the invention, the combination of the long pitch with relatively long axial length allows for precise deployment, for example, relatively long axial movement is transmitted to small amounts of deployment. For example, axial compression of the device by about 10 mm, or about 20 mm or about 30 mm, translates into a radial expansion to a diameter of about 2 mm, or about 3 mm, or about 4 mm, or other combinations of compression and expansion are possible. In an exemplary embodiment of the invention, the control in deployment allows the application of sufficient force by the expansion element to the vessel wall to anchor the microcatheter in placed without damaging the vessel wall.

FIG. 20 is a simplified diagram of guidewire 322 piercing atheroma 326 and helix 310 in the retracted state, in accordance with an exemplary embodiment of the invention. Optionally, FIG. 20 follows FIG. 19 in a possible sequence.

In an exemplary embodiment of the invention, helix 310 is retractable back to the predeployment state. Optionally, axially displacing outer tube 314 in a proximal direction retracts helix 310 from the expanded state (e.g., FIG. 19).

FIG. 21 is a simplified diagram of inner tube 320 piercing lesion 326, in accordance with an exemplary embodiment of the invention. Optionally, FIG. 21 follows FIG. 20 in a possible sequence.

In an exemplary embodiment of the invention, inner tube 302 is axially displaced in a distal direction towards atheroma 326. Tip 304 is advanced into atheroma 326 and optionally through atheroma 326. Potentially, inner tube 302 is advanced through atheroma 326, for example, useful in performing procedures distally to atheroma 326.

A potential advantage of attaching helix 310 to outer tube 314 but not to inner tube 302 is to allow for movement of inner tube 302 that is not hindered by helix 310. For example, tube 302 is advanced within atheroma 326.

In some embodiments, inner tube 302 is advanced through atheroma 326 while helix 310 is held outside of atheroma 326. Alternatively or additionally, tube 302 is advanced through atheroma 326 together with helix 310 (e.g., at the same time or after tube 302). Potentially, helix 310 is used to perform other procedures distal to atheroma 326.

Optionally, helix 310 is expanded inside atheroma 326. Potentially, expansion of helix 310 expands the lumen through atheroma 326, for example, expanding the vessel lumen to allow adequate blood flow through atheroma 326 to prevent ischemia of downstream tissues.

Some Alternative Deployment Element Embodiments

Figure 37A:
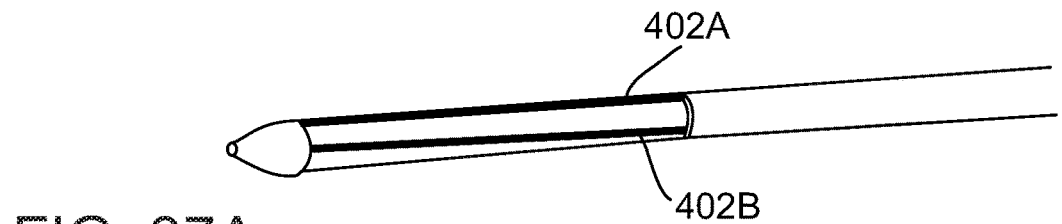
FIGS. 37A to 37B are simplified diagrams of another embodiment of the deployment element, in accordance with an exemplary embodiment of the invention.
Figure 37B:
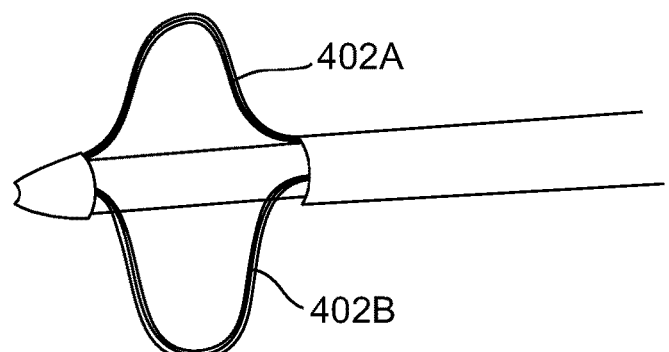

FIG. 37A is a simplified diagram of a deployment element comprising one or more bars 402A-B, in accordance with some embodiments of the invention. Bars 402A-B are shown in the retracted state. In some embodiments, the bars are arranged circumferentially around the inner tube, for example, approximately equally spaced apart. FIG. 37B is a simplified diagram of the bars 402A-B of FIG. 37A in the expanded state. In some embodiments, an axially directed force at the tips of the bars is translated into a radial expansion, for example, the formation of one or more curves in the bars. Potentially, the use of bars achieves the highest ratio of axial compression to radial expansion.

Figure 38A:
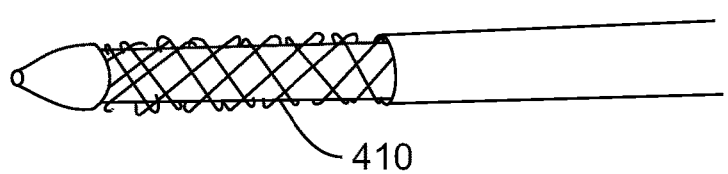
FIGS. 38A to 38B are simplified diagrams of another embodiment of the deployment element, in accordance with an exemplary embodiment of the invention.
Figure 38B:
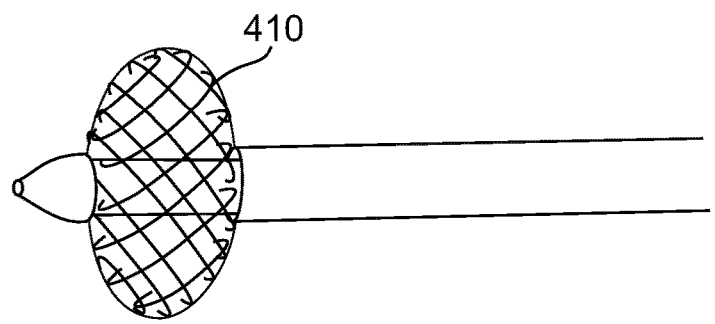

FIG. 38A is a simplified diagram of a deployment element comprising a braid 410, in accordance with some embodiments of the invention. Braid 410 is shown in the retracted state. In some embodiments, braid 410 comprises a plurality of wires braided together. In some embodiments, braid 410 is a sleeve encircling at least some of the outer circumference of the inner tube of the microcatheter. FIG. 38B shows braid 410 in the expanded state. In some embodiments, an axially directed force at the edges of the braid is translated into a radial expansion. Potentially, the use of braids reduces or prevents trauma to the vessel wall by distributing the applied force over a relatively larger surface area.

Optionally, bars 402A-B and/or braid 410 are made out of a memory material, for example, Nitinol.

Handle for Deploying the Exterior Deployment Device

Figure 35A:
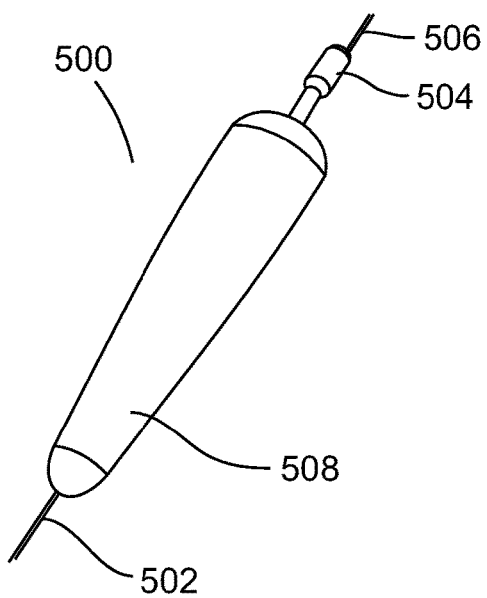
FIGS. 35A to 35B are simplified diagrams of a handle for use with the microcatheter of FIG. 34D.
Figure 35B:
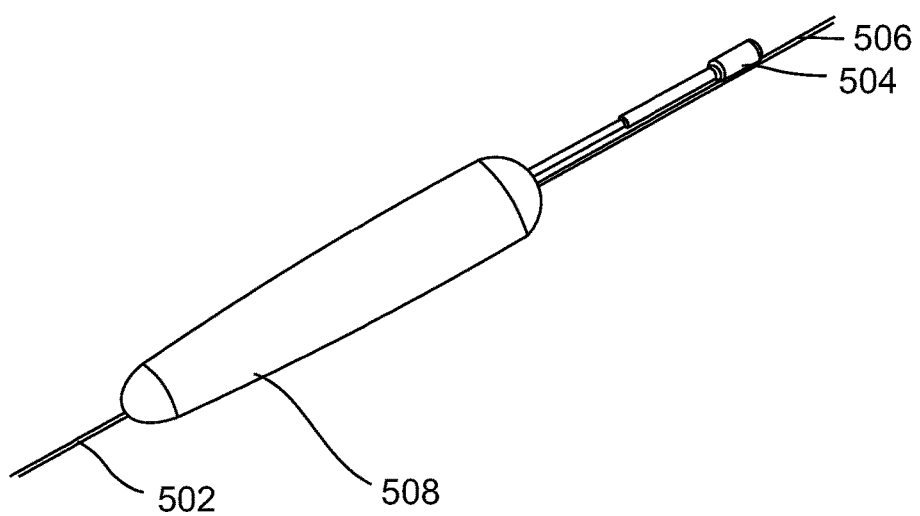

FIGS. 35A-C are simple diagrams of an optional handle 500 for use with the microcatheter having the external deployment element, in accordance with some embodiments of the invention. In some embodiments, handle allows for precise control over the axial distance between the inner and outer tubes, for example, precise to within about, or about 0.5 mm, or about 1 mm, or about 2 mm, or about 5 mm, or about 10 mm, or other smaller, intermediate or larger dimensions. In some embodiments, control over the axial distance provides control of the radial expansion of the deployment element, for example, according to the ratios as described herein.

In some embodiments, handle 500 is connected to an inner tube 506 of the microcatheter, for example, handle 500 is rigidly attached to inner tube 506. Holding handle 500 still maintains the position of inner tube 506.

In some embodiments, a button 504 controls the axial displacement of an external tube 502. Optionally, turning button 504 urges external tube 502 forward or backwards. In some embodiments, the forward force of external tube 502 applies an axial force on the deployment element (e.g., against the flange of the inner tube). In some embodiments, turning button 504 radially expands and/or deforms the deployment element.

In some embodiments, a user output (e.g., progress indicator 508) visually displays the amount of expansion of the deployment element. For example, the button and the indicator are calibrated so that turning of the button moves a bar, indicating the percent and/or distance of deployment. Other user outputs are possible, for example, an electronic screen and/or audio output (e.g., recorded message).

In some embodiments, axially displacing button 504 displaces outer tube 502. Optionally, the displacements are directly corresponding. For example, moving button 504 from a standard position (e.g., FIG. 35A) to an axially retracted position (e.g., FIG. 35B) axially moves outer tube 502 in a proximal axial movement relative to inner tube 506. Optionally, the axial movement of button 504 axially displaces the displacement element, for example, as shown with reference to FIG. 19 (e.g., standard position) and FIG. 20 (e.g., axially retracted). In some embodiments, button can be moved no more than about 10 mm, or about 20 mm, or about 30 mm, or about 40 mm, or about 50 mm, or other smaller, intermediate or larger distances.

In some embodiments, a second button and/or button 504 lock the relative position of outer tube 502 and inner tube 506. Optionally or additionally, the position of the guidewire is locked.

Optionally, a luer is assembled on the distal end of the microcatheter (e.g., inner tube 506), for example, to allow injection of fluids such as contrast.

Some potential advantages of the handle include; ability to deploy the element and control the microcatheter using one hand, visual feedback on the deployment, prevention of over-retraction of the outer catheter.

Some Exemplary Microcatheter Tip Designs

Figure 23:
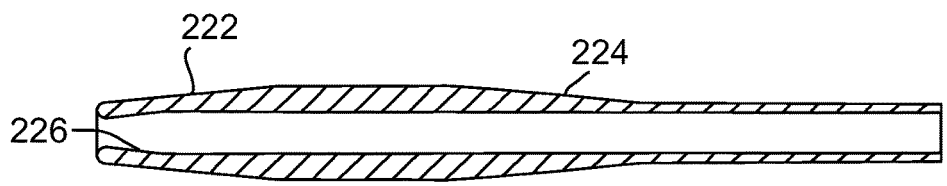
FIG. 23 is a cross section of a simplified diagram of a design of the microcatheter tip, in accordance with an exemplary embodiment of the invention.
Figure 24:
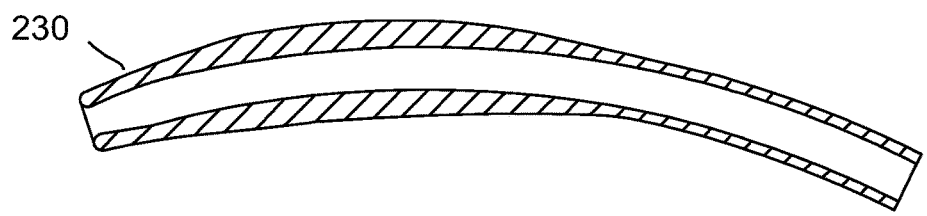
FIG. 24 is a cross section of another simplified diagram of a design of the microcatheter tip, in accordance with an exemplary embodiment of the invention.
Figure 25:
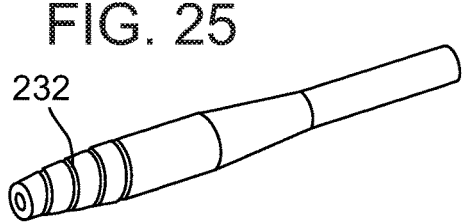
FIG. 25 is a cross section of yet another simplified diagram of a design of the microcatheter tip, in accordance with an exemplary embodiment of the invention.

FIGS. 23-25 are simple diagrams of some distal tips for the inner tube of the microcatheter, in accordance with some embodiments of the invention.

FIG. 23 shows an inner tube tip having a cone shaped surface 222 at the distal tip and an adjoining cone shaped surface 224 slightly proximally thereof (e.g., diameters from distal tip; narrow, increasing in diameter, narrowing again). Potentially, the cone shaped surfaces 222 and/or 224 allow the distal tip of the inner tube to slide in and out of the atheroma.

In some embodiments, the cone shaped surface 224 is sufficiently steep to act as a flange to prevent the deployment element (e.g., helix) from sliding off and/or to act as a stop to allow the helix to expand.

In some embodiments, the inner diameter of the lumen of the internal tube 226 decreases in near proximity to the tip. The decrease in diameter is, for example, about 5%, about 10%, about 25%, about 33%, or other smaller, intermediate or larger percentages. The length of the decrease is, for example, about 1 mm from the most distal tip, or about 3 mm, or about 5 mm, or other smaller, intermediate or larger lengths. In some embodiments, the decrease in diameter is shaped and/or sized to provide for geometric continuity of the outer tube over the guidewire. Potentially, the continuity helps the outer tube tip slide into the atheroma more easily.

FIG. 24 is a simple diagram of an angular distal tip 230 of the internal tube, in accordance with some embodiments of the invention. The angle of tip 230 relative to the long axis of the proximal portion of the internal tube is, for example, about 5 degrees, or about 15 degrees, or about 30 degrees, or other smaller, intermediate or larger angles. Potentially, the angular tip supports directing the guidewire in a curved (e.g., bifurcating) vessel anatomy. Another potential advantage of the angular tip is helping to direct a guide wire into the sub-intima tissue, for example, in a re-entry or re-canalization vascular procedure.

FIG. 25 is a simplified diagram of a distal tip of the inner tube having one or more helical grooves 232, in accordance with some embodiments of the invention. Potentially, grooves 232 allow for a screw-like penetration of the atheroma and/or forward motion inside the atheroma.

Other shapes of distal tips are possible, for example, convex, concave and/or combinations of the shapes described and/or other shapes. The selection of a suitable distal tip depends on, for example, the anatomy of the blood vessel and/or the makeup of the lesion.

In some embodiments, the tips of FIGS. 23-25 are made from biocompatible materials, not necessarily limiting example include; polymers, metal, silicon (optionally mixed with radio-opaque powder such as tungsten particles).

Method of Using the Microcatheter with Exterior Deployment Device

Figure 36:
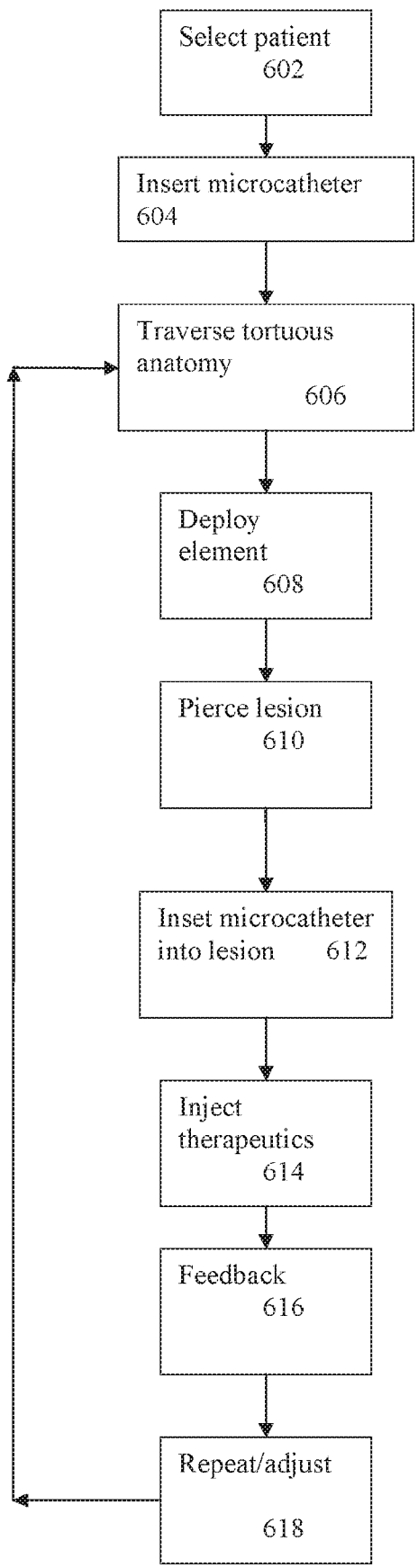
FIG. 36 is a flowchart of a method of treating a patient using the deployment element, in accordance with an exemplary embodiment of the invention.

FIG. 36 is a method of treating a patient (e.g., human or other mammals) using the microcatheter with deployment element, in accordance with an exemplary embodiment of the invention. The method is not necessarily limited to the devices described herein, as other devices can be used. The method is also not necessarily limited to the boxes described below, as some boxes are optional and other orders of boxes are also possible.

Optionally, at box 602, a patient is selected for treatment with the microcatheter having the deployment device, in accordance with an exemplary embodiment of the invention. The selecting is done, for example, by the treating physician, for example, by the neurointerventional radiologist, interventional cardiologist, or others performing procedures.

In some embodiments, the patient is selected for treatment based on a lesion blocking blood flow through a blood vessel. Not necessarily limiting examples of lesions include; embolus, thrombus, atheroma. In some embodiments, the size of the blood vessel is no more than, for example, about 1 mm, about 2 mm, about 3 mm, about 4 mm, about 6 mm, or other smaller, intermediate or larger sizes. Not necessarily limiting examples of blood vessels include; coronary arteries, brain blood vessels. Alternatively or additionally, the patient is selected for treatment using the microcatheter based on tortuous anatomy, in which case the microcatheter is used to traverse the anatomy to reach the target.

Optionally, at box 604, the microcatheter having the deployment device is inserted into the body of the patient, in accordance with an exemplary embodiment of the invention. Optionally, the arterial system is accessed. Alternatively, the venous system is accessed. Some not necessarily limiting examples of access sites include; femoral artery/vein, radial artery, jugular vein.

Optionally, at box 606, the microcatheter with the deployment device is used to traverse tortuous anatomy, (e.g., as found in the blood vessels of the brain), in accordance with an exemplary embodiment of the invention. For example, as described in the section "EXEMPLARY METHODS OF TRAVERSING TORTUOUS VESSELS".

Alternatively or additionally, the microcatheter is used to provide fine movements, for example, when in close proximity to the lesion, for example, as described in the section "EXEMPLARY METHOD OF TRAVERSING A VESSEL".

Figure 32A:
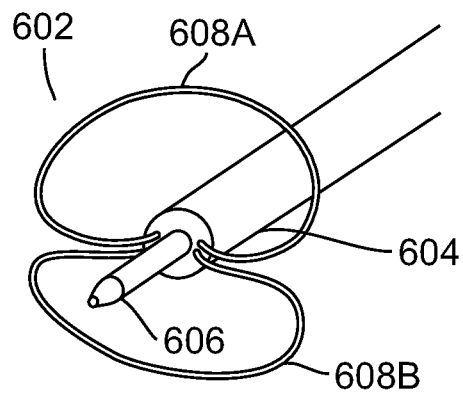
FIGS. 32A to 32C are simplified diagrams of a deployment element shaped to bring the microcatheter near to the lesion, in accordance with an exemplary embodiment of the invention.
Figure 32B:
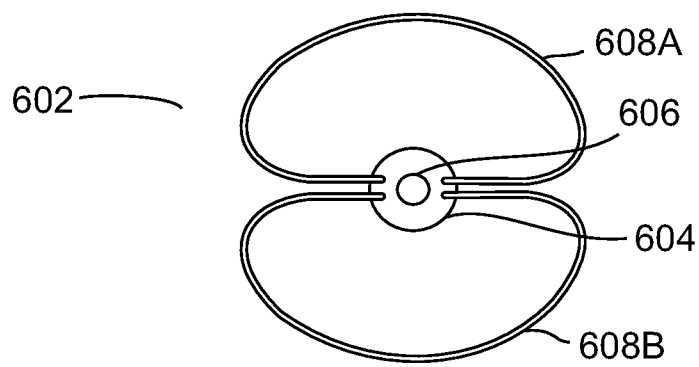
Figure 32C:
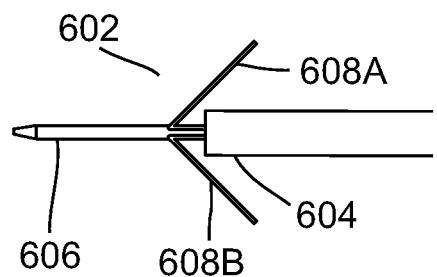

At box 608, the deployment device is deployed and the guidewire and/or microcatheter tip (e.g., inner tube) is placed in near proximity to the lesion, in accordance with an exemplary embodiment of the invention. For example, as described with reference to FIG. 19. For example, no more than about 1 mm away, or 3 mm away, or 5 mm away, or 10 mm away, or 15 mm away, or 20 mm away, or other smaller, intermediate or larger distances. For example, the device as in FIG. 18 is used. For example, the device as in FIGS. 32A-C is used.

Optionally, the deployed device positions the guidewire and/or inner microcatheter tube approximately in the center of the vessel. Optionally or additionally, the guidewire and/or microcatheter inner tube are positioned parallel to the long axis of the blood vessel. Optionally or additionally, the force applied against the vessel walls by the deployment device provides anchoring of at least some of the microcatheter (e.g., outer tube). For example, natural movements of the operator do not displace the deployment device in the vessel.

In some embodiments, deployment occurs by applying an axial compression force to the deployment element, for example, by pushing the outer tube with respect to the inner tube. The force radially expands and/or deforms the element to the deployed configuration. Alternatively, in some embodiments, deployment occurs by removal of an outer encasing sheath. Optionally, a device is used to assist with the deployment, for example, the handle as described with reference to FIGS. 35A-B.

Optionally, at box 610, the lesion is pierced with the guidewire, in accordance with an exemplary embodiment of the invention. For example, as described with reference to FIG. 20.

Optionally, at box 612, the microcatheter (e.g., inner tube) is inserted into the lesion. For example, as described with reference to FIG. 21. Optionally or additionally, the deployment element is inserted into the lesion and optionally expanded in the lesions, for example, as described with reference to FIG. 21.

Optionally, at box 614, one or more ablation techniques are used, in accordance with some embodiments of the invention. Optionally, one or more therapeutics are injected. For example, injection occurs proximal to the lesion, inside the lesion and/or outside the lesion.

One major obstacle is the initial penetration into the occlusion, which may take place through the occlusion's cortex. When using the deployable element, additional ablation techniques may be used through a carefully centered internal lumen to ease the initial, and potentially also the ongoing, penetration into the occlusion.

The ablation technique may be applied using chemical/pharmacological means (e.g. by injecting a proteolytic material), or electrical means, or ultra-sonic means.

FIG. 31 is a simplified diagram showing the microcatheter injecting one or more therapeutic substances 280 in the blood vessel, in accordance with some embodiments of the invention. In some embodiments, the device, when suitably centered, can be used to deliver plaque-directed local pharmacologic treatments, for example, aimed at priming and/or softening the 'proximal fibrous cap' in order to facilitate a wire crossing through the proximal segment of the lesion.

Pharmacologic agents that can be delivered and provide for plaque modification include: 1) collagenous matrix degradation agent (i.e. collagenase), 2) microvessel producers (e.g. thrombolytic agents, contrast injection, angiogenic growth factors used as either proteins or gene-based angiogenic promoters such as vascular endothelial growth factors, hypoxia inducing factors, nitrous oxide, angiopoietin, leptin, etc.).

Alternatively, in some embodiments, the microcatheter injects materials for vessel embolization (e.g., liver chemoembolization using particles, coil embolization to seal a GI bleed). In a some embodiments, the force exerted by the deployment device against the blood vessel wall is sufficient to prevent or reduce sliding backwards of the catheter tip during the embolization procedure, for example, due to momentum of the discharged materials. In some embodiments, the deployment device is secured inside the blood vessel so that kick back from release of the materials does not cause inaccurate positioning. Potentially, non-target embolization complications are reduced or prevented.

Alternatively or additionally, other ablation techniques are used, for example, radiofrequency ablation, for example, as described with reference to FIGS. 14A-B.

Optionally, at 616, feedback about the deployment and/or procedure is obtained.

Optionally, feedback is obtained about the extent of the expansion of the deployment device. Not necessarily limiting examples include; from the visual indicator on the handle (e.g., FIGS. 35A-B), using fluoroscopy from the radio-opaque markers (e.g., FIG. 23).

In some embodiments, the expansion element is used as feedback. Optionally, in such embodiments, the expansion element is made out of a memory metal (e.g., nitinol) and is formed into the helix in the natural and/or unconstrained, and/or expands with a predefined force. Optionally, the expansion element is attached to both inner and outer tubes. Optionally, applying tension to the expansion element compresses the element for the delivery configuration, for example, by proximally pulling the outer tube relative to the inner tube. In some embodiments, once in position, the expansion element is allowed to expand to the predefined configuration (e.g., helix), for example, by releasing the tension. In some embodiments, the amount of expansion of the expansion element relative to the total possible expansion is used as the feedback, for example, by looking at the visual output on the handle, and/or using the ratio of the radial expansion to axial compression ratio.

Optionally, at 618, one or more boxes are repeated, in accordance with some embodiments of the invention. Optionally, one or more of 606, 608, 610, 612, 614 and/or 616 are repeated, for example, to treat a second (or more) lesion in the blood vessels.

Optionally, one or more boxes are repeated with adjustments. For example, injection of agents to soften the plaque (e.g., as in 614) is performed before insertion of the guidewire into the lesion (e.g., as in 610). For example, if on feedback (e.g., as in 616) the hole through the lesion by the guidewire (e.g., as in 610) is not sufficiently large, the microcatheter can be inserted into the lesion (e.g., as in 612).

Exemplary Deployment Device for Lesion Proximity

FIGS. 32A-32C are views of a deployment device 602 shaped for placing a distal tip 604 of the microcatheter in near proximity to the lesion, in accordance with an exemplary embodiment of the invention. FIG. 32A is an isometric view, FIG. 32B is a face on view and FIG. 32C is a side view.

Optionally distal tip 604 comprises an inner tube of the microcatheter. Optionally, the inner tube comprises at least one lumen sized for a guidewire 606 to pass therethrough.

In an exemplary embodiment of the invention, device 602 comprises of at least one deployment member attached to tip 604, for example, two loops 608A-B, or 4 loops, or other intermediate or larger number of loops. Loops 608A-B comprise of at least a segment for positioning against the vessel wall, for example, a curved surface sized and/or shaped to fit against the vessel wall.

In an exemplary embodiment of the invention, a planar surface of loops 608A-B is positioned at an angle towards tip 604. The angle of the plane of loops 608A-B relative to the surface of tip 604 is, for example, about 0 degrees to about 90 degrees, or about 30 degrees, or about 45 degrees, or about 60 degrees, or about 75 degrees. Potentially, the angle prevents or reduces interference of loops 608A-B with the plaque and allows positioning of the tip in close proximity to the plaque. In practice, the angle prevents or reduces back movement of tip 604, as back movement is resisted by the angled loops.

In an exemplary embodiment of the invention, loops 608A-B are made out of a memory material, for example, Nitinol. Optionally, loops 608A-B are made out of wires, for example, Nitinol wires.

In an exemplary embodiment of the invention, loops 608A-B are deployed by an outer sheath or external tube, for example, the sheath encasing the tip 604 and loops 608A-B is moved proximally relative to the encased loops 608A-B. Optionally or additionally, loops 608A-B are retracted by moving the encasing sheath distally to the position encasing tip 604 and loops 608A-B.

In an exemplary embodiment of the invention, nitinol wires 608A-B are attached to the inner tube (e.g., tip 604). Optionally, the inner tube comprises a plurality of lumens, and wires 608A-B are attached inside the lumens, for example, by using an adhesive. Alternatively, wires 608A-B are attached to tip 604, not necessarily limiting examples include; heating the internal tube and melting the tube over the Nitinol wires 608A-B, using a shrinking tube which is assembled over the wires and attaches wires 608A-B once the shrinking tube has been heated and shrunk. A potential advantage of attaching the wires to the tip is that the wires are torqued when the loop is shrunk, for example, as opposed to reacting with bending strains. Without being bound to the theory, bending stresses tend to be non-homogenous in nature, for example, relatively higher and/or concentrated in certain locations, which potentially lead to earlier failure of the structure. In contrast, torque beam and/or struts tend to develop homogenous internal stresses along the structure. The distribution of the external load may allow for the structure to be able to resist higher loads.

In some embodiments, the internal tube (including tip 604) is made out of a relatively flexible material (e.g., compared to metal), for example, polymer.

Some Additional Exemplary Deployment Device Embodiments

Figure 33A:
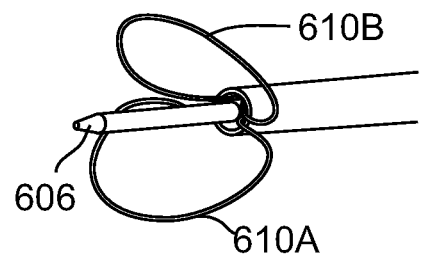
FIGS. 33A to 33C are simplified diagrams of another embodiment of the deployment element, in accordance with an exemplary embodiment of the invention.
Figure 33B:
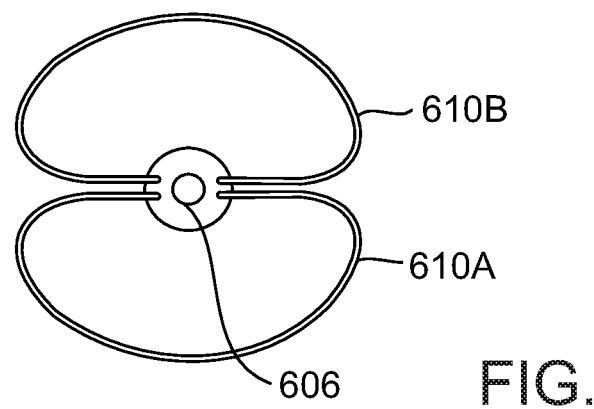
Figure 33C:
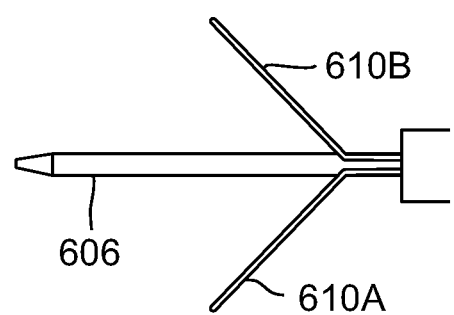

FIGS. 33A-C illustrate another embodiment of the deployment device using loops as described with reference to FIGS. 32A-C, loops 610A-B being angled in a forward direction (e.g., distally and/or towards the lesion). FIG. 33A is an isometric view, FIG. 32B is a face on view and FIG. 32C is a side view.

In some embodiments, the planar surface of loops 610A-B having an angle relative to the surface of guidewire 606 ranging from 0 to 90 degrees, for example, about 15 degrees, about 30 degrees, about 45 degrees, about 60 degrees, about 75 degrees, or other smaller, intermediate or larger angles.

Potentially, the forward angling loops prevent or reduce forward motion of the microcatheter tip towards the lesion, for example, preventing inadvertent dislodging of the lesion.

Reference is now made to FIG. 10 which is a simplified schematic diagram illustrating an alternative configuration of the deployment element 114, in accordance with some embodiments of the invention. In the case of FIG. 10 the deployment element comprises a distal tip made up of a single helical length 142. Operation is the same as for the device of FIG. 2 and FIG. 10 illustrates the deployed geometry.

Reference is now made to FIG. 11 which is a simplified schematic diagram illustrating an alternative configuration of the deployment element 114, in accordance with some embodiments of the invention. In the case of FIG. 11 the deployment element comprises a distal tip made up of three fins or petals 152 which in the deployed state open out into a tripod configuration. Operation is the same as for the device of FIG. 2 and FIG. 11 illustrates the deployed geometry.

It is noted that guide wire 50 may pass longitudinally through the whole lumen. Alternatively the wire may pass through a side slit through the external tube and into the flexible inner tube, thus enabling the use of a relatively shorter guide wire.

Exemplary Method of Traversing a Vessel

FIG. 12A-12D are four simplified diagrams that demonstrate a tool according to a some embodiments of the invention, which consists of two flexible tubes, one being assembled over the other, and wherein the tubes enable self-driving of the tool through a blood vessel to clear the blood vessel of plaque during an angioplasty. An external flexible tube 140 comprises external deployment element 142. An internal deployment element 144 comprises internal deployment element 146.

As shown in FIG. 12A initially external deploying element 142 is opened while afterwards internal flexible tube 144 is driven forward, and the distal deploying element 146 is deployed (FIG. 12B). At this point, external or proximal deploying element 142 is shrunk into its external tube 140. Then the proximal flexible element is driven forward and deployed at a new forward position immediately behind the forward position reached by the distal deploying element 146, as shown in FIG. 12C.

Finally distal deployable element 146 is shrunk into its internal tube, and the cycle is repeated with the tool advancing forward.

Optionally, the above stages can be repeated over and over to drive the tool longitudinally along the blood vessel. Optionally a proximal handle may be provided to sequentially switch between the above stages automatically.

Optionally, one of the two deploying elements, either the proximal or the distal element, comprises a balloon.

A potential advantage of such a two-deploying-element mechanism is to direct/drive a guidewire through a substantially long occlusion, such as the kinds that are typically encountered in the peripheral vessels and peripheral angioplasty.

Some Exemplary Microcatheter Tip Designs

Reference is now made to FIG. 13, which is a simplified diagram showing a variation of the tool, in accordance with some embodiments. An elongate continuous external tube 160 has either a cone-like distal tip 162 and/or a screw tip with threads 164. Potentially, the tips enable better accessibility through the blood vessel to approach and subsequently pass through into the occlusion.

Figure 14A:
FIG. 14A illustrates an embodiment wherein the guide wire includes an electrode for ablation of occlusions.

FIG. 14A is a simplified schematic diagram showing a guide wire 170 with a deployment element according to the present embodiment and also including an internal electrode 171 for treating the cortex using a magnetic or RF field. The deployable elements and the associated elongate body are covered by the electrical isolation of the external tube 172, and the tube and the electrodes are combined with an electrical power source, for example an RF power source. In use, an electrical ablating field is generated in between the deployable element and the guide wire. The electrical field may be confined or substantially confined inside the boundaries of the deployable element, and may be mostly concentrated at the centered guide wire tip.

Figure 14B:
FIG. 14B illustrates a variation of the embodiment of FIG. 14A wherein two electrodes are provided in the guide wire.

Reference is now made to FIG. 14B which is an alternative embodiment of the guide wire of FIG. 14A. In FIG. 14B, a double electrode guide wire may be used following centering by the deployable element. In that case the guidewire's electrodes 180, 182, are connected with the electrical power source and the electrical ablation occurs only at the guidewire's distal tip 184. Again the field is confined by the deployment element and is effective in deploying against the cortex at the beginning of the occlusion.

Exemplary Kit

In some embodiments of the invention, the deployment element is sold separately from the microcatheter, for example as a kit or a set. Optionally, many different deployment elements are available, for example, different expansion sizes (e.g., for different diameter vessels), different lengths and/or number of contact points (e.g., for irregular vessels).

In one example, the kit comprises: a deployment element at the end of a long wire or catheter for insertion through a lumen into the vasculature, for example, as described with reference to FIGS. 1, 32A, and/or 33A. Optionally, different shapes of the deployment element are available, for example, as described with reference to FIGS. 10 and 11. Optionally or additionally, the deployment element is sold with a handle for expansion and retraction, for example, as described with reference to FIGS. 6 and/or 7. Optionally or additionally, special catheters (having the lumen) having ends with different features are also sold, for example, as described with reference to FIGS. 13, 14A, and/or 14B.

In another example, the kit comprises: different types of deployment elements adapted to be placed around the outer portion of the inner tube, for example, as shown in FIGS. 34B, 37A, 37B, 38A, 38B. Optionally or additionally, the kit comprises the inner tube (e.g., FIG. 34A), optionally different ends are available for the inner tube (e.g., FIGS. 23-25. Optionally or additionally, the kit comprises the outer tube (e.g., FIG. 34C). Optionally or additionally, the kit comprises the control handle (e.g., FIGS. 35A, 35B).

Exemplary Methods of Traversing Tortuous Vessels

FIGS. 26 to 30 illustrate a possible sequence of a method of using the microcatheter having the distal deployment device to navigate tortuous vessels (e.g., brain arterial vasculature), in accordance with an exemplary embodiment of the invention. Optionally, the microcatheter is used to help pass an outer catheter (e.g., encasing sheath) through the challenging anatomy. Some not necessarily limiting examples of procedure requiring traversing through challenging anatomy include; interventional neuroradiology procedures, liver vessel embolization, GI bleeding control).

FIG. 26 is a simplified diagram of vessel anatomy to help understand why passing an outer catheter 706 over a guidewire 708 is difficult or impossible. Passing catheter 706 over a microcatheter positioned over guidewire 708 is also difficult or impossible. Note guidewire 708 is positioned in a highly curved branch vessel 704 off main vessel 702. In practice, the problem is that the user of a flexible and/or floppy microcatheter (e.g., which is capable of passing through the vessel curvature) may not provide sufficient rigidity to allow outer catheter 706 to pass over the microcatheter. For example, the microcatheter tends to retract upon sliding outer catheter 706 thereon. Alternatively, the use of a microcatheter that is rigid enough to let catheter 706 slide over without retracting may be too rigid to pass through the vessel curvature.

FIG. 27 illustrates the use of the microcatheter to help traverse curved branch vessel 704. For example, using microcatheter 318 as described with reference to FIG. 18. Microcatheter 318 is shown with tip 304 of inner tube 302 having been threaded over guidewire 708 and positioned in branch vessel 704. External tube 314 and/or helix 310 are in main vessel 702.

Optionally, at least a distal end of inner tube 302 is made out of a material sufficiently flexible and/or floppy to navigate tight turns (e.g., branch of vessels 702 and 704). For example, the most distal 10 mm, or 20 mm, or 30 mm, or 50 mm, or other smaller, intermediate or longer lengths. Optionally or additionally, at least a distal end of outer tube 314 is made of a similar material. Not necessarily limiting examples of materials include; nylon, soft Pbax.

FIG. 28 illustrates helix 310 (e.g., or other deployment device) having been pushed into branch vessel 704. Catheter 706 is positioned in main vessel 702.

In some embodiments, FIG. 28 follows in sequence after FIG. 27, that is, first inner tube 302 is pushed around the curve into vessel 704, followed by helix 310 and outer tube 310. Alternatively, FIG. 28 does not follow FIG. 27 (e.g., the process of FIG. 27 is omitted). For example, tip 304 (of the inner tube), helix 310 and outer tube 314 are all pushed together around the curve and into vessel 704. The ability to skip over the method of FIG. 27 depends, for example, on the preference of the physician in performing the procedure and/or on the flexibility of the materials used in the microcatheter.

FIG. 29 illustrates the deployment of the deployment device (e.g., helix 310) inside branch vessel 704. In an exemplary embodiment of the invention, deployed helix 310 anchors within branch vessel 704, providing sufficient support to advance catheter 706 over outer tube 314 and from main vessel 702 into branch vessel 704. In some embodiments, some tension is applied to outer tube 314 and/or inner tube 302, for example, from outside the body of the patient, for example, by the handle. Potentially, the tension helps to prevent deformation of the microcatheter as sheath 706 is passed over.

In an exemplary embodiment of the invention, helix 310 has a sufficiently low cross sectional area (when in the expanded state) relative to the blood vessel to prevent significant reduction in blood flow to downstream tissues.

For example, helix 310 blocks no more than about 25% of blood flow, or about 33% of blood flow, or about 50% of blood flow, or about 70% of blood flow, or other smaller, intermediate or larger flow percentages. Potentially, deploying helix 310 does not cause dangerous ischemia to the tissues, for example, to the brain during neuro-radiology procedures. Alternatively, in some embodiments, helix 310 has a sufficiently high cross sectional area relative to the blood vessel to significantly reduce blood flow. Potentially, the reduction in blood flow is desirable, for example, in embolization procedures, for example, to prevent escape of the embolization materials to healthy tissues.

Reference is now made to FIG. 15, which is a simplified schematic diagram illustrating another technique for use with some embodiments, in which a resilient guide wire 190 is positioned inside a curved vessel, such as a blood vessel, near an occlusion. As shown the guide wire follows the maximal curved pathway on the vessel's wall, since the guide wire is intrinsically straight and the resilience attempts to restore the guidewire to its intrinsic straight shape. Thus the distal end of the guidewire tends to try to contact the vessel's wall, with the inherent risk of damaging the epithelium or even perforating the vessel's wall.

Reference is now made to FIG. 16, a simplified schematic diagram, in which an alternative micro catheter 200 based on a flexible tube is shown, in accordance with some embodiments. Optionally, deployment head 202 is located at the distal tip of the micro-catheter 200. As shown in FIG. 16, when using flexible tube micro-catheter 200, deployment head 202 centers the guidewire. Potentially, reducing the risk of harming or even perforating the vessel wall.

Reference is now made to FIG. 17, which is a simplified schematic diagram showing an alternative centering device in which a deployable element 204 is opened at an angle relative to an elongate tube 206 within blood vessel 208, in accordance with some embodiments. A potential advantage, is that despite the steep angle of the guide wire, using the deployment element, it is still able to approach occlusion 2100 while centered in the vessel.

For simplicity, the above description relates to the vascular field and to angioplasty and like procedures, including peripheral angioplasty. However the same centering technique may be used in other medical procedures involving threading a device through a tube, for example balloon eustachian tuboplasty, fallopian tuboplasty, etc. and others.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A microcatheter for insertion within a vessel comprising:
   a first tube sized and shaped for surrounding at least a portion of a guidewire;
   a second tube at least partially disposed around said first tube, said second tube slidingly associated with said first tube;
   a deployment element disposed around at least a portion of said first tube distal to said second tube and slidingly associated with said first tube, the sliding association allowing the first tube to be axially advanced separately from the second tube while the deployment element remains in a radially unexpanded state;
   said first tube having at least a portion interfering with said deployment element such that distal travel of said slidingly associated deployment element is limited, wherein said interfering portion of the first tube is not attached to the deployment element; and
   said second tube having at least a portion interfering with said deployment element such that proximal travel of said deployment element is limited;
   said deployment element being configured to reversibly expand radially upon axial compression between said interfering portions of said first and second tubes; and
   said expanded deployment element configured to contact a wall of said vessel so that at least part of said portion of said first tube distal to said second tube is radially positioned within a central 33% of the diameter of said vessel.

2. The microcatheter as in claim 1, wherein said deployment element is disposed around at least a portion of an exterior surface of said first tube without blocking one or more lumens in said microcatheter.

3. The microcatheter as in claim 1, wherein said deployment element is arranged relative to said second tube so that sliding said second tube axially displaces said deployment element relative to said first tube.

4. The microcatheter as in claim 1, wherein said deployment element comprises a helix.

5. The microcatheter as in claim 1, wherein said first tube comprises a tip shaped for insertion into a lesion.

6. The microcatheter as in claim 1, wherein a maximum ratio expansion in a radial direction of said deployment element is at least 4:1.

7. The microcatheter as in claim 1, wherein a surface of said deployment element is flush with a surface of said second tube.

8. The microcatheter as in claim 1, wherein said deployment element has a cross sectional area in an expanded state expanded to contact the wall of the vessel that is small enough so as not to block more than 50% of blood flow in said vessel in an amount that cause ischemia to downstream tissues.

9. The microcatheter as in claim 1, wherein said expanded deployment element is arranged to align a portion of said first tube in parallel with a long axis of said vessel.

10. The microcatheter as in claim 1, wherein at least 3 cm of a distal end of said first tube is made out of a material more flexible than material of said second tube proximal to a predetermined axial location.

11. The microcatheter as in claim 1, further comprising a handle adapted to control precise movements of said first tube relative to said second tube.

12. The microcatheter as in claim 1, wherein said deployment element comprises a strut configured to contact said vessel wall at a small number of contact locations so that said deployment element adjusts to an uneven vessel wall.

13. The microcatheter as in claim 1, wherein a central axis of the distal end of said radially positioned at least part of said portion of said first tube is angled away from a local axis of said vessel by about 15 to about 60 degrees.

14. The microcatheter as in claim 1, wherein a length of said second tube is flexible.

15. The microcatheter according to claim 1, wherein said deployment element comprises at least one marker made of a radio-opaque material, said at least one marker being configured to be positioned at an outer limit of the radial expansion of said deployment element in an expanded configuration.

16. The microcatheter according to claim 1, wherein a distal portion of said second tube is axially advanceable without axially advancing said first tube.

17. The microcatheter according to claim 1, wherein the element comprises nitinol.

18. The microcatheter according to claim 1, wherein the portion of the first tube interfering with the deployment element comprises a flange.

19. The microcatheter according to claim 18, wherein:
   said deployment element comprises a helix of one or more struts disposed around said first tube;
   the helix comprises reinforced edges at distal and proximal ends of the one or more struts for positioning against the respective interfering portions of the first and second tubes; and
   the one or more struts comprise one or more radio-opaque markers positioned therealong.

20. The microcatheter according to claim 1, wherein the deployment element comprises a helix of one or more struts extending between a distal and a proximal end of the deployment element; wherein the distal end of the deployment element is unattached to either the first tube or the second tube; and wherein an increase in radial dimension due to the radial expansion is larger at a location approximately at a longitudinal middle of the one or more struts than at both a distal end and a proximal end of the one or more struts.

21. The microcatheter according to claim 1, wherein the axial compression comprises contact between a distal edge of the deployment element and the interfering portion of the first tube.

22. The microcatheter according to claim 1, wherein the sliding association allows the first tube to be axially advanced separately from the second tube while the deployment element remains in a radially maximally unexpanded state.

23. The microcatheter according to claim 1, wherein the deployment element is self-collapsing.

24. A method of traversing a tortuous vessel region using a microcatheter having a deployment element (310) thereon, said method comprising:
   advancing a distal end of a first tube (302) of the microcatheter over a guidewire spanning a bend in said tortuous region so that said distal end is positioned distally of said tortuous region, said advancing being without advancing the deployment element (310);
   advancing a second tube (314) of the microcatheter together with said deployment element (310) at a distal end of the second tube over said first tube (302), so that said deployment element (310) is positioned distally to said bend in said tortuous region, and beyond an outer sheath (706), while the deployment element (310) remains in an unexpanded state;

expanding said deployment element (310) to anchor said second tube (314) in a vessel and;

advancing the outer sheath (706) over said second tube (314) towards said deployment element (310) and through the bend of said tortuous vessel region using the anchored second tube (314) as a guide.

25. The method of claim 24, wherein the expanding comprises axial compression of the deployment element between said first and second tubes.

* * * * *